United States Patent
Merrick et al.

(10) Patent No.: US 8,628,542 B2
(45) Date of Patent: Jan. 14, 2014

(54) MEDIAN LOBE DESTRUCTION APPARATUS AND METHOD

(75) Inventors: Daniel Merrick, Dublin, CA (US);
Joseph Catanese, III, San Leandro, CA (US); Ling-Kang Tong, Fremont, CA (US); Floria Cheng, San Francisco, CA (US); Michael Gearhart, Fremont, CA (US); Matthew McLean, San Francisco, CA (US); Brian Y. Tachibana, Oakland, CA (US); Ben Thompson, San Carlos, CA (US); James W. Niederjohn, San Jose, CA (US)

(73) Assignee: NeoTract, Inc., Pleasanton, CA (US)

( * ) Notice: Subject to any disclaimer, the term of this patent is extended or adjusted under 35 U.S.C. 154(b) by 286 days.

(21) Appl. No.: 12/979,075

(22) Filed: Dec. 27, 2010

(65) Prior Publication Data
US 2011/0166564 A1    Jul. 7, 2011

Related U.S. Application Data

(63) Continuation-in-part of application No. 12/852,243, filed on Aug. 6, 2010, now Pat. No. 8,333,776, and a continuation-in-part of application No. 12/512,674, filed on Jul. 30, 2009, now Pat. No. 8,216,254, which is a continuation-in-part of application No. 11/775,162, filed on Jul. 9, 2007, which is a continuation-in-part of application No. 11/671,914, filed on Feb. 6, 2007, now Pat. No. 8,157,815, which is a continuation-in-part of application No. 11/492,690, filed on Jul. 24, 2006, now Pat. No. 7,896,891, which is a continuation-in-part of application No. 11/318,246, filed on Dec. 22, 2005, now Pat. No. 7,645,286, which is a continuation-in-part of application No. 11/134,870, filed on May 20, 2005, now Pat. No. 7,758,594.

(60) Provisional application No. 61/084,937, filed on Jul. 30, 2008.

(51) Int. Cl.
*A61B 17/10* (2006.01)

(52) U.S. Cl.
USPC ....................................................... 606/139

(58) Field of Classification Search
USPC ......... 606/139, 144–146, 148–151, 153, 157, 606/232
See application file for complete search history.

(56) References Cited

U.S. PATENT DOCUMENTS

| 659,422 A | 10/1900 | Shidler |
| 780,392 A | 1/1905 | Wanamaker et al. |

(Continued)

FOREIGN PATENT DOCUMENTS

| DE | 10159470 | 6/2003 |
| EP | 0246836 | 12/1991 |

(Continued)

OTHER PUBLICATIONS

Richard Berges et al., "Alternative Minimalinvasive Therapien Beim Benignen Prostatasyndrom", Medizin, Jg. 104, Heft 37, Sep. 14, 2007.

(Continued)

*Primary Examiner* — Gregory Anderson
(74) *Attorney, Agent, or Firm* — Steptoe & Johnson LLP

(57) ABSTRACT

A system and associated method for altering or destroying tissues and anatomical or other structures in medical applications for the purpose of treating diseases or disorders. In one aspect, the system includes a device configured to deploy devices for altering the lobes of a prostate.

12 Claims, 16 Drawing Sheets

(56) References Cited

U.S. PATENT DOCUMENTS

| | | | |
|---|---|---|---|
| 789,467 A | 5/1905 | West | |
| 2,579,192 A | 12/1951 | Kohl | |
| 2,646,298 A | 7/1953 | Leary | |
| 2,697,624 A | 12/1954 | Thomas et al. | |
| 2,734,299 A | 2/1956 | Masson | |
| 2,825,592 A | 3/1958 | Semple | |
| 3,326,586 A | 6/1967 | Frost et al. | |
| 3,470,834 A | 10/1969 | Bone | |
| 3,521,918 A | 7/1970 | Hammond | |
| 3,664,345 A | 5/1972 | Dabbs et al. | |
| 3,713,680 A | 1/1973 | Pagano | |
| 3,716,058 A | 2/1973 | Tanner, Jr. | |
| 3,756,638 A | 9/1973 | Stockberger | |
| 3,873,140 A | 3/1975 | Bloch | |
| 3,875,648 A | 4/1975 | Bone | |
| 3,931,667 A | 1/1976 | Merser et al. | |
| 3,976,079 A | 8/1976 | Samuels et al. | |
| 4,006,747 A | 2/1977 | Kronenthal et al. | |
| 4,210,148 A | 7/1980 | Stivala | |
| 4,235,238 A | 11/1980 | Ogiu et al. | |
| 4,291,698 A | 9/1981 | Fuchs et al. | |
| 4,409,974 A | 10/1983 | Freedland | |
| 4,493,323 A | 1/1985 | Albright et al. | |
| 4,513,746 A | 4/1985 | Aranyi | |
| 4,621,640 A | 11/1986 | Mulhollan et al. | |
| 4,657,461 A | 4/1987 | Smith | |
| 4,669,473 A | 6/1987 | Richards et al. | |
| 4,705,040 A | 11/1987 | Mueller et al. | |
| 4,714,281 A | 12/1987 | Peck | |
| 4,738,255 A | 4/1988 | Goble et al. | |
| 4,741,330 A | 5/1988 | Hayhurst | |
| 4,744,364 A | 5/1988 | Kensey | |
| 4,750,492 A | 6/1988 | Jacobs | |
| 4,762,128 A | 8/1988 | Rosenbluth | |
| 4,823,794 A | 4/1989 | Pierce | |
| 4,899,743 A | 2/1990 | Nicholson et al. | |
| 4,926,860 A | 5/1990 | Stice et al. | |
| 4,946,468 A | 8/1990 | Li | |
| 4,955,913 A | 9/1990 | Robinson | |
| 4,968,315 A | 11/1990 | Gatturna | |
| 5,002,550 A | 3/1991 | Li | |
| 5,041,129 A | 8/1991 | Hayhurst et al. | |
| 5,046,513 A | 9/1991 | Gatturna et al. | |
| 5,053,046 A | 10/1991 | Janese | |
| 5,080,660 A | 1/1992 | Buelna | |
| 5,100,421 A | 3/1992 | Christoudias | |
| 5,123,914 A | 6/1992 | Cope | |
| 5,129,912 A | 7/1992 | Noda et al. | |
| 5,159,925 A * | 11/1992 | Neuwirth et al. | 607/105 |
| 5,192,303 A | 3/1993 | Gatturna et al. | |
| 5,203,787 A | 4/1993 | Noblitt et al. | |
| 5,207,672 A | 5/1993 | Roth et al. | |
| 5,217,470 A | 6/1993 | Weston | |
| 5,217,486 A | 6/1993 | Rice et al. | |
| 5,234,454 A | 8/1993 | Bangs | |
| 5,236,445 A | 8/1993 | Hayhurst et al. | |
| 5,258,015 A | 11/1993 | Li et al. | |
| 5,267,960 A | 12/1993 | Hayman et al. | |
| 5,269,802 A | 12/1993 | Garber | |
| 5,269,809 A | 12/1993 | Hayhurst et al. | |
| 5,300,099 A * | 4/1994 | Rudie | 607/101 |
| 5,322,501 A | 6/1994 | Mahmud-Durrani | |
| 5,330,488 A | 7/1994 | Goldrath | |
| 5,334,200 A | 8/1994 | Johnson | |
| 5,336,240 A | 8/1994 | Metzler et al. | |
| 5,354,271 A | 10/1994 | Voda | |
| 5,358,511 A | 10/1994 | Gatturna et al. | |
| 5,364,408 A | 11/1994 | Gordon | |
| 5,366,490 A | 11/1994 | Edwards et al. | |
| 5,368,599 A | 11/1994 | Hirsch et al. | |
| 5,370,646 A | 12/1994 | Reese et al. | |
| 5,380,334 A | 1/1995 | Torrie et al. | |
| 5,391,182 A | 2/1995 | Chin | |
| 5,403,348 A | 4/1995 | Bonutti | |
| 5,405,352 A | 4/1995 | Weston | |
| 5,411,520 A | 5/1995 | Nash et al. | |
| 5,417,691 A | 5/1995 | Hayhurst | |
| 5,435,805 A | 7/1995 | Edwards et al. | |
| 5,470,337 A | 11/1995 | Moss | |
| 5,472,446 A | 12/1995 | de la Torre | |
| 5,480,406 A | 1/1996 | Nolan et al. | |
| 5,499,994 A | 3/1996 | Tihon et al. | |
| 5,501,690 A | 3/1996 | Measamer et al. | |
| 5,507,754 A | 4/1996 | Green et al. | |
| 5,522,846 A | 6/1996 | Bonutti | |
| 5,531,763 A | 7/1996 | Mastri et al. | |
| 5,536,240 A | 7/1996 | Edwards et al. | |
| 5,540,704 A | 7/1996 | Gordon et al. | |
| 5,545,171 A | 8/1996 | Sharkey et al. | |
| 5,545,178 A | 8/1996 | Kensey et al. | |
| 5,550,172 A | 8/1996 | Regula et al. | |
| 5,554,162 A | 9/1996 | DeLange | |
| 5,554,171 A | 9/1996 | Gatturna et al. | |
| 5,562,689 A | 10/1996 | Green et al. | |
| 5,569,305 A | 10/1996 | Bonutti | |
| 5,571,104 A | 11/1996 | Li | |
| 5,573,540 A | 11/1996 | Yoon | |
| 5,578,044 A | 11/1996 | Gordon et al. | |
| 5,591,177 A | 1/1997 | Lehrer | |
| 5,593,421 A | 1/1997 | Bauer | |
| 5,611,515 A | 3/1997 | Benderev et al. | |
| 5,626,614 A | 5/1997 | Hart | |
| 5,630,824 A | 5/1997 | Hart | |
| 5,647,836 A | 7/1997 | Blake, III et al. | |
| 5,665,109 A | 9/1997 | Yoon | |
| 5,667,486 A | 9/1997 | Mikulich et al. | |
| 5,667,488 A * | 9/1997 | Lundquist et al. | 604/22 |
| 5,669,917 A | 9/1997 | Sauer et al. | |
| 5,690,677 A | 11/1997 | Schmiedling et al. | |
| 5,697,950 A | 12/1997 | Fucci et al. | |
| 5,707,394 A | 1/1998 | Miller et al. | |
| 5,716,368 A | 2/1998 | de la Torre et al. | |
| 5,718,717 A | 2/1998 | Bonutti | |
| 5,725,556 A | 3/1998 | Moser et al. | |
| 5,725,557 A | 3/1998 | Gatturna et al. | |
| 5,733,306 A | 3/1998 | Bonutti | |
| 5,741,276 A | 4/1998 | Poloyko et al. | |
| 5,746,753 A | 5/1998 | Sullivan et al. | |
| 5,749,846 A | 5/1998 | Edwards et al. | |
| 5,752,963 A | 5/1998 | Allard et al. | |
| 5,782,862 A | 7/1998 | Bonutti | |
| 5,782,864 A | 7/1998 | Lizardi | |
| 5,800,445 A | 9/1998 | Ratcliff et al. | |
| 5,807,403 A | 9/1998 | Beyar et al. | |
| 5,810,848 A | 9/1998 | Hayhurst | |
| 5,814,072 A | 9/1998 | Bonutti | |
| 5,830,179 A | 11/1998 | Mikus et al. | |
| 5,830,221 A | 11/1998 | Stein | |
| 5,845,645 A | 12/1998 | Bonutti | |
| 5,846,254 A | 12/1998 | Schulze et al. | |
| 5,861,002 A | 1/1999 | Desai | |
| 5,868,762 A | 2/1999 | Cragg et al. | |
| 5,873,891 A | 2/1999 | Sohn | |
| 5,879,357 A | 3/1999 | Heaton et al. | |
| 5,897,574 A | 4/1999 | Bonutti | |
| 5,899,911 A | 5/1999 | Carter | |
| 5,899,921 A | 5/1999 | Caspari et al. | |
| 5,904,679 A | 5/1999 | Clayman | |
| 5,904,696 A | 5/1999 | Rosenman | |
| 5,908,428 A | 6/1999 | Scirica et al. | |
| 5,919,198 A | 7/1999 | Graves, Jr. et al. | |
| 5,919,202 A | 7/1999 | Yoon | |
| 5,921,986 A | 7/1999 | Bonutti | |
| 5,928,252 A | 7/1999 | Steadman et al. | |
| 5,931,844 A | 8/1999 | Thompson et al. | |
| 5,944,739 A | 8/1999 | Zlock et al. | |
| 5,948,001 A | 9/1999 | Larsen | |
| 5,948,002 A | 9/1999 | Bonutti | |
| 5,954,057 A | 9/1999 | Li | |
| 5,954,747 A | 9/1999 | Clark | |
| 5,964,732 A | 10/1999 | Willard | |
| 5,971,447 A | 10/1999 | Steck, III | |
| 6,010,514 A | 1/2000 | Burney et al. | |
| 6,011,525 A | 1/2000 | Piole | |

(56) References Cited

U.S. PATENT DOCUMENTS

| | | |
|---|---|---|
| 6,030,393 A | 2/2000 | Corlew |
| 6,033,413 A | 3/2000 | Mikus et al. |
| 6,033,430 A | 3/2000 | Bonutti |
| 6,036,701 A | 3/2000 | Rosenman |
| 6,048,351 A | 4/2000 | Gordon et al. |
| 6,053,908 A | 4/2000 | Crainich et al. |
| 6,056,722 A | 5/2000 | Jayaraman |
| 6,056,772 A | 5/2000 | Bonutti |
| 6,068,648 A | 5/2000 | Cole et al. |
| 6,080,167 A | 6/2000 | Lyell |
| 6,086,608 A | 7/2000 | Ek et al. |
| 6,110,183 A | 8/2000 | Cope |
| 6,117,160 A | 9/2000 | Bonutti |
| 6,117,161 A | 9/2000 | Li et al. |
| 6,120,539 A | 9/2000 | Eldridge et al. |
| 6,139,555 A | 10/2000 | Hart et al. |
| RE36,974 E | 11/2000 | Bonutti |
| 6,143,006 A | 11/2000 | Chan |
| 6,152,935 A | 11/2000 | Kammerer et al. |
| 6,159,207 A * | 12/2000 | Yoon ........................ 606/41 |
| 6,159,234 A | 12/2000 | Bonutti et al. |
| 6,200,329 B1 | 3/2001 | Fung et al. |
| 6,206,895 B1 | 3/2001 | Levinson |
| 6,228,096 B1 | 5/2001 | Marchand |
| 6,258,124 B1 | 7/2001 | Darois et al. |
| 6,261,302 B1 | 7/2001 | Voegele et al. |
| 6,270,530 B1 | 8/2001 | Eldridge et al. |
| 6,280,460 B1 | 8/2001 | Bolduc et al. |
| 6,290,711 B1 | 9/2001 | Caspari et al. |
| 6,312,448 B1 | 11/2001 | Bonutti |
| 6,319,263 B1 | 11/2001 | Levinson |
| 6,322,112 B1 | 11/2001 | Duncan |
| 6,332,889 B1 | 12/2001 | Sancoff et al. |
| 6,398,795 B1 | 6/2002 | McAlister et al. |
| 6,425,900 B1 | 7/2002 | Knodel et al. |
| 6,428,562 B2 | 8/2002 | Bonutti |
| 6,436,107 B1 | 8/2002 | Wang et al. |
| 6,461,355 B2 | 10/2002 | Svejkovsky et al. |
| 6,482,235 B1 | 11/2002 | Lambrecht et al. |
| 6,488,691 B1 | 12/2002 | Carroll et al. |
| 6,491,707 B2 | 12/2002 | Makower et al. |
| 6,494,888 B1 | 12/2002 | Laufer et al. |
| 6,500,195 B2 | 12/2002 | Bonutti |
| 6,506,190 B1 | 1/2003 | Walshe |
| 6,506,196 B1 | 1/2003 | Laufer |
| 6,517,569 B2 | 2/2003 | Mikus et al. |
| 6,527,702 B2 | 3/2003 | Whalen et al. |
| 6,527,794 B1 | 3/2003 | McDevitt et al. |
| 6,530,932 B1 | 3/2003 | Swayze et al. |
| 6,533,796 B1 | 3/2003 | Sauer et al. |
| 6,547,725 B1 | 4/2003 | Paolitto et al. |
| 6,551,328 B2 | 4/2003 | Kortenbach |
| 6,551,333 B2 | 4/2003 | Kuhns et al. |
| 6,565,578 B1 | 5/2003 | Peifer et al. |
| 6,569,187 B1 | 5/2003 | Bonutti et al. |
| 6,572,626 B1 | 6/2003 | Knodel et al. |
| 6,572,635 B1 | 6/2003 | Bonutti |
| 6,572,653 B1 | 6/2003 | Simonson |
| 6,592,609 B1 | 7/2003 | Bonutti |
| 6,596,013 B2 | 7/2003 | Yang et al. |
| 6,626,913 B1 | 9/2003 | McKinnon et al. |
| 6,626,916 B1 | 9/2003 | Yeung et al. |
| 6,626,919 B1 | 9/2003 | Swanstrom |
| 6,629,534 B1 | 10/2003 | St. Goar et al. |
| 6,641,592 B1 | 11/2003 | Sauer et al. |
| 6,656,182 B1 | 12/2003 | Hayhurst |
| 6,660,023 B2 | 12/2003 | McDevitt et al. |
| 6,663,589 B1 | 12/2003 | Halevy |
| 6,663,639 B1 | 12/2003 | Laufer et al. |
| 6,699,263 B2 | 3/2004 | Cope |
| 6,706,047 B2 | 3/2004 | Trout et al. |
| 6,709,493 B2 | 3/2004 | DeGuiseppi et al. |
| 6,715,804 B2 | 4/2004 | Beers |
| 6,719,709 B2 | 4/2004 | Whalen et al. |
| 6,730,112 B2 | 5/2004 | Levinson |
| 6,736,823 B2 | 5/2004 | Darois et al. |
| 6,736,854 B2 | 5/2004 | Vadurro et al. |
| 6,740,098 B2 | 5/2004 | Abrams et al. |
| 6,767,037 B2 | 7/2004 | Wenstrom, Jr. |
| 6,770,076 B2 | 8/2004 | Foerster |
| 6,773,438 B1 | 8/2004 | Knodel et al. |
| 6,773,441 B1 | 8/2004 | Laufer et al. |
| 6,790,213 B2 | 9/2004 | Cherok et al. |
| 6,802,846 B2 | 10/2004 | Hauschild et al. |
| 6,821,282 B2 | 11/2004 | Perry et al. |
| 6,821,285 B2 | 11/2004 | Laufer et al. |
| 6,821,291 B2 | 11/2004 | Bolea et al. |
| 6,835,200 B2 | 12/2004 | Laufer et al. |
| 6,905,475 B2 | 6/2005 | Hauschild et al. |
| 6,908,473 B2 | 6/2005 | Skiba et al. |
| 6,926,732 B2 | 8/2005 | Derus et al. |
| 6,951,565 B2 | 10/2005 | Keane et al. |
| 6,986,775 B2 | 1/2006 | Morales et al. |
| 6,991,596 B2 | 1/2006 | Whalen et al. |
| 6,991,647 B2 | 1/2006 | Jadhav |
| 6,997,940 B2 | 2/2006 | Bonutti |
| 7,001,327 B2 | 2/2006 | Whalen et al. |
| 7,008,381 B2 * | 3/2006 | Janssens ........................ 600/564 |
| 7,011,688 B2 | 3/2006 | Gryska et al. |
| 7,015,253 B2 | 3/2006 | Escandon et al. |
| 7,048,698 B2 | 5/2006 | Whalen et al. |
| 7,048,747 B2 | 5/2006 | Arcia et al. |
| 7,060,077 B2 | 6/2006 | Gordon et al. |
| 7,081,126 B2 | 7/2006 | McDevitt et al. |
| 7,083,638 B2 | 8/2006 | Foerster |
| 7,087,073 B2 | 8/2006 | Bonutti |
| 7,089,064 B2 | 8/2006 | Manker et al. |
| 7,090,690 B2 | 8/2006 | Foerster et al. |
| 7,093,601 B2 | 8/2006 | Manker et al. |
| 7,105,004 B2 | 9/2006 | Dicesare et al. |
| 7,108,655 B2 | 9/2006 | Whalen et al. |
| 7,141,038 B2 | 11/2006 | Whalen et al. |
| 7,153,314 B2 | 12/2006 | Laufer et al. |
| 7,179,225 B2 | 2/2007 | Shluzas |
| 7,226,558 B2 | 6/2007 | Nieman et al. |
| 7,232,448 B2 | 6/2007 | Battles et al. |
| 7,288,063 B2 | 10/2007 | Petros et al. |
| 7,303,108 B2 | 12/2007 | Shelton, IV |
| 7,320,701 B2 | 1/2008 | Haut et al. |
| 7,322,974 B2 | 1/2008 | Swoyer et al. |
| 7,326,221 B2 | 2/2008 | Sakamoto et al. |
| 7,334,822 B1 | 2/2008 | Hines, Jr. |
| 7,340,300 B2 | 3/2008 | Christopherson et al. |
| 7,399,304 B2 | 7/2008 | Gambale et al. |
| 7,402,166 B2 | 7/2008 | Feigl |
| 7,416,554 B2 | 8/2008 | Lam et al. |
| 7,417,175 B2 | 8/2008 | Oda et al. |
| 7,481,771 B2 | 1/2009 | Fonseca et al. |
| 7,553,317 B2 | 6/2009 | Weisenburgh, II et al. |
| 7,608,108 B2 | 10/2009 | Bhatnagar et al. |
| 7,658,311 B2 | 2/2010 | Boudreaux |
| 7,674,275 B2 | 3/2010 | Martin et al. |
| 7,727,248 B2 | 6/2010 | Smith et al. |
| 2001/0044639 A1 | 11/2001 | Levinson |
| 2002/0095154 A1 | 7/2002 | Atkinson et al. |
| 2002/0107540 A1 | 8/2002 | Whalen et al. |
| 2002/0128684 A1 | 9/2002 | Foerster |
| 2002/0161382 A1 | 10/2002 | Neisz et al. |
| 2002/0193809 A1 | 12/2002 | Meade |
| 2003/0109769 A1 | 6/2003 | Lowery et al. |
| 2003/0191497 A1 | 10/2003 | Cope |
| 2003/0199860 A1 | 10/2003 | Loeb et al. |
| 2003/0204195 A1 | 10/2003 | Keane et al. |
| 2003/0236535 A1 | 12/2003 | Onuki et al. |
| 2004/0030217 A1 | 2/2004 | Yeung et al. |
| 2004/0043052 A1 | 3/2004 | Hunter et al. |
| 2004/0078046 A1 | 4/2004 | Barzell et al. |
| 2004/0193191 A1 | 9/2004 | Starksen et al. |
| 2004/0193194 A1 | 9/2004 | Laufer et al. |
| 2004/0194790 A1 | 10/2004 | Laufer et al. |
| 2004/0243178 A1 | 12/2004 | Haut et al. |
| 2004/0243179 A1 | 12/2004 | Foerster |
| 2004/0243180 A1 | 12/2004 | Donnelly |
| 2004/0243227 A1 | 12/2004 | Starksen et al. |

(56) References Cited

U.S. PATENT DOCUMENTS

| | | |
|---|---|---|
| 2004/0260345 A1 | 12/2004 | Foerster |
| 2005/0010203 A1 | 1/2005 | Edwards et al. |
| 2005/0055087 A1 | 3/2005 | Starksen |
| 2005/0065550 A1 | 3/2005 | Starksen et al. |
| 2005/0107811 A1 | 5/2005 | Starksen et al. |
| 2005/0107812 A1 | 5/2005 | Starksen et al. |
| 2005/0154401 A1 | 7/2005 | Weldon et al. |
| 2005/0165272 A1 | 7/2005 | Okada et al. |
| 2005/0177181 A1 | 8/2005 | Kagan et al. |
| 2005/0203344 A1 | 9/2005 | Orban et al. |
| 2005/0203550 A1 | 9/2005 | Laufer et al. |
| 2005/0216078 A1 | 9/2005 | Starksen et al. |
| 2005/0267405 A1 | 12/2005 | Shah |
| 2005/0273138 A1 | 12/2005 | To et al. |
| 2006/0025750 A1 | 2/2006 | Starksen et al. |
| 2006/0025784 A1 | 2/2006 | Starksen et al. |
| 2006/0025789 A1 | 2/2006 | Laufer et al. |
| 2006/0025819 A1 | 2/2006 | Nobis et al. |
| 2006/0030884 A1 | 2/2006 | Yeung et al. |
| 2006/0058817 A1 | 3/2006 | Starksen et al. |
| 2006/0089646 A1 | 4/2006 | Bonutti |
| 2006/0167477 A1 | 7/2006 | Arcia et al. |
| 2006/0265042 A1 | 11/2006 | Catanese, III et al. |
| 2006/0282081 A1 | 12/2006 | Fanton et al. |
| 2007/0049929 A1 | 3/2007 | Catanese, III |
| 2007/0049970 A1 | 3/2007 | Belef et al. |
| 2007/0060931 A1 | 3/2007 | Hamilton et al. |
| 2007/0088362 A1 | 4/2007 | Bonutti et al. |
| 2007/0112385 A1 | 5/2007 | Conlon |
| 2007/0142846 A1 | 6/2007 | Catanese, III et al. |
| 2007/0173888 A1 | 7/2007 | Gertner et al. |
| 2007/0260259 A1 | 11/2007 | Fanton et al. |
| 2008/0009888 A1 | 1/2008 | Ewers et al. |
| 2008/0021445 A1 | 1/2008 | Elmouelhi et al. |
| 2008/0033488 A1 | 2/2008 | Catanese, III et al. |
| 2008/0039894 A1 | 2/2008 | Catanese, III et al. |
| 2008/0045978 A1 | 2/2008 | Kuhns et al. |
| 2008/0058710 A1 | 3/2008 | Wilk |
| 2008/0065120 A1 | 3/2008 | Zannis et al. |
| 2008/0082113 A1 | 4/2008 | Bishop et al. |
| 2008/0086172 A1 | 4/2008 | Martin et al. |
| 2008/0091220 A1 | 4/2008 | Chu |
| 2008/0091237 A1 | 4/2008 | Schwartz et al. |
| 2008/0119874 A1 | 5/2008 | Merves |
| 2008/0154378 A1 | 6/2008 | Pelo |
| 2008/0195145 A1 | 8/2008 | Bonutti et al. |
| 2008/0208220 A1 | 8/2008 | Shiono et al. |
| 2008/0269737 A1 | 10/2008 | Elmouelhi et al. |
| 2010/0010631 A1 | 1/2010 | Otte et al. |
| 2010/0030262 A1 | 2/2010 | McLean et al. |
| 2010/0114162 A1 | 5/2010 | Bojarski et al. |
| 2010/0286106 A1 | 11/2010 | Gat et al. |
| 2010/0286679 A1 | 11/2010 | Hoey et al. |

FOREIGN PATENT DOCUMENTS

| | | |
|---|---|---|
| EP | 0632999 | 1/1995 |
| EP | 1016377 | 7/2000 |
| EP | 1082941 | 3/2005 |
| EP | 1006909 | 1/2007 |
| EP | 1852071 | 11/2007 |
| EP | 0464480 | 1/2008 |
| EP | 1670361 | 4/2008 |
| EP | 1884198 | 6/2008 |
| EP | 1884199 | 6/2008 |
| EP | 1331886 | 12/2008 |
| FR | 2750031 | 6/1996 |
| JP | 58036559 | 3/1983 |
| RU | 2062121 | 6/1996 |
| RU | 2112571 | 6/1998 |
| RU | 2128012 | 3/1999 |
| RU | 2221501 | 1/2004 |
| SU | 0825094 | 4/1981 |
| WO | WO 92/10142 | 6/1992 |
| WO | WO 93/04727 | 3/1993 |
| WO | WO 93/15664 | 8/1993 |
| WO | WO 0230335 | 4/2002 |
| WO | WO 03/039334 | 5/2003 |
| WO | WO03/077772 | 9/2003 |
| WO | WO2004019787 | 3/2004 |
| WO | WO2004017845 | 4/2004 |
| WO | WO2004030569 | 4/2004 |
| WO | WO2004103189 | 12/2004 |
| WO | WO2007064906 | 6/2007 |
| WO | WO2007053516 | 10/2007 |
| WO | WO2008006084 | 1/2008 |
| WO | WO2008043044 | 4/2008 |
| WO | WO2008043917 | 4/2008 |
| WO | WO2009009617 | 1/2009 |
| WO | WO2010011832 | 1/2010 |

OTHER PUBLICATIONS

Rudolf Hartung, et al., "Instrumentelle Therapie der benignen Prostatahyperplasie", Medizin, Deutsches Arzteblatt 97, Heft 15, Apr. 14, 2000.

Klaus Hofner, et al., "Operative Therapie des benignen Prostatasyndroms", Medizin, Dtsch Arztebl 2007; 104(36):A 2424-9.

R. Hubmann, "Geschichte der transurethralen Prostataeingriffe", Geschichte der Medizin, Urologe [B] 2000 40:152-160.

U. Jonas, et al., "Benigne Prostatahyperplasie", Der Urologe 2006—[Sonderheft] 45:134-144.

O.A. Bacharova, et al., "The Effect of Rhodiolae Rosea Extract on Incidence Rate of Superficial Bladder Carcinoma Relapses", Kozin 1995.

S. Kruck, et al., "Aktuelle Therapiemoglichkeiten des Benignen Prostata-Syndroms", J Urol Urogynakol 2009; 16 (1):19-22.

Osamu Miyake, "Medical Examination and Treatment for BPH", Pharma Med vol. 22, No. 3, 2004, p. 97-103.

Ohashi Teruhisa, "Urinary Dysfunction by Lower Urinary Tract Obstruction in Male", Pharma Medica vol. 8, No. 8, p. 35-39, 1990.

O. Reich, et al. "Benignes Prostatasyndrom (BPS)", Der Urologe A Issue vol. 45, No. 6, Jun. 2006, p. 769-782.

Daito Takashi, "Low-Invasive Treatment for BPH", Medico vol. 34, No. 10, p. 366-369, 2002.

Trapeznikov et al., "New Technologies in the Treatment of Benign Prostatic Hyperplasia", Urologia Nefrol (Mosk) Jul.-Aug. 1996, (4):41-47.

Koyanagi Tomohiko, et al., "Surgery View of 21st Century", Urological Surgery, vol. 84, No. 1, p. 47-53, 2001.

Borzhievski, et al., "Tactics of the Surgical Treatment of Patients With Prostatic Adenoma and Acute Urinary Retention", Urologia Nefrol (Mosk), Jan.-Feb. 1987, (1):39-43.

Sharp, Howard T., M.D., et al., "Instruments and Methods—The 4-S Modification of the Roeder Knot: How to Tie It", Obstetrics & Gynecology, p. 1004-1006, vol. 90, No. 6, Dec. 1997.

P. Schauer et al. "New applications for endoscopy: the emerging field of endoluminal and transgastric bariatric surgery," Surgical Endoscopy, Accepted Jun. 7, 2006.

Yeung, Jeff, "Treating Urinary Stress Incontinence Without Incision With Endoscopic Suture Anchor and Approximating Device," Aleeva Medical, Inc., 2007.

\* cited by examiner

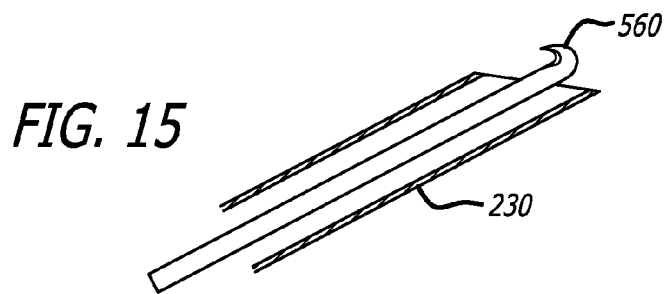
FIG. 15
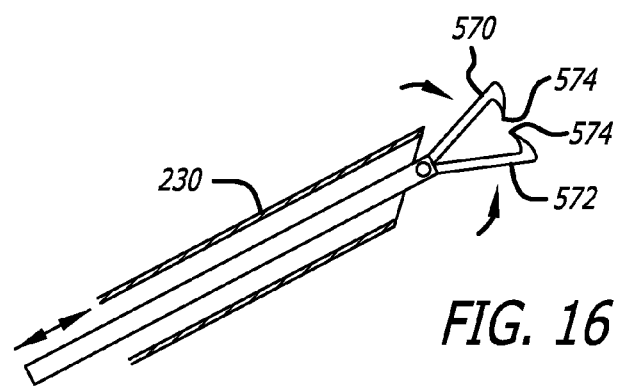
FIG. 16
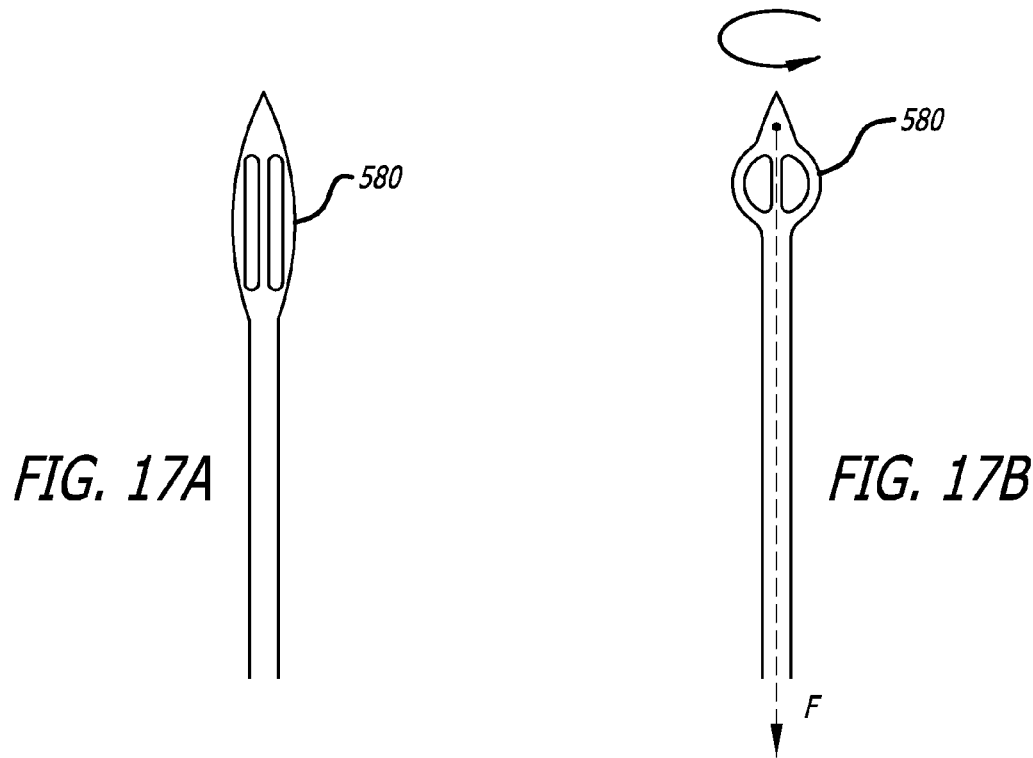
FIG. 17A
FIG. 17B

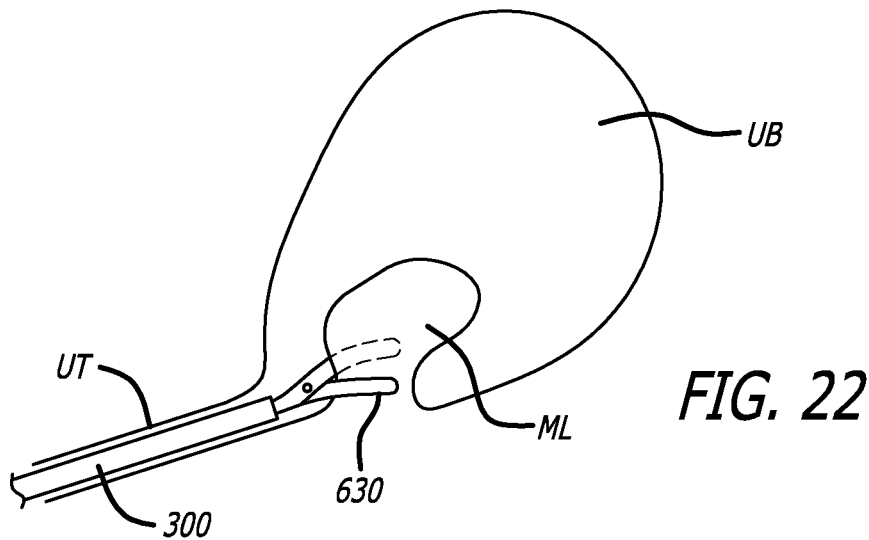
FIG. 22
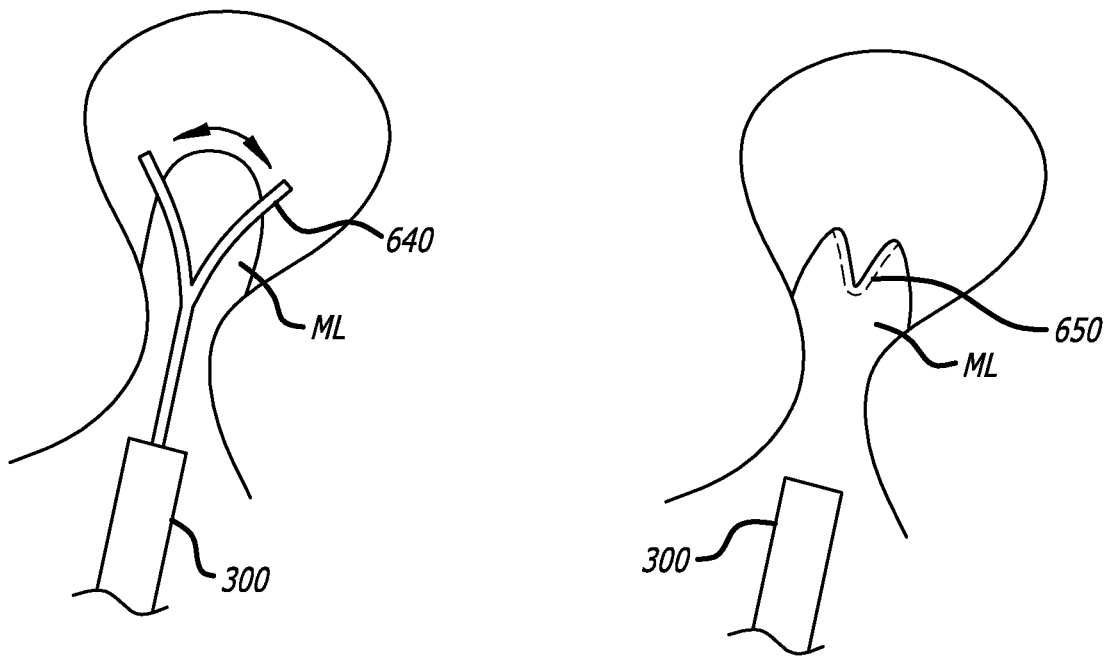
FIG. 23A
FIG. 23B

MEDIAN LOBE DESTRUCTION APPARATUS AND METHOD

CROSS-REFERENCES TO RELATED APPLICATIONS

This application is a continuation-in-part of: 1) U.S. patent application Ser. No. 12/852,243, now U.S. Pat. No. 8,333,776, filed Aug. 6, 2010; 2) U.S. patent application Ser. No. 12/512,674, now U.S. Pat. No. 8,216,254, filed Jul. 30, 2009 which claims the benefit of Provisional Application Ser. No. 61/084,937; 3) copending U.S. patent application Ser. No. 11/775,162, filed Jul. 9, 2007: 4) U.S. patent application Ser. No. 11/671,914, now U.S. Pat. No. 8,157,815, filed Feb. 6, 2007; 5) U.S. patent application Ser. No. 11/492,690, now U.S. Pat. No. 7,896,891, filed on Jul. 24, 2006; 6) copending U.S. patent application Ser. No. 11/833,660, filed on Aug. 3, 2007, which is a continuation of U.S. patent application Ser. No. 11/318,246, now U.S. Pat. No. 7,645,286, filed on Dec. 20, 2005; and 7) U.S. patent application Ser. No. 11/838,036 filed on Aug. 13, 2007, which is a continuation of U.S. patent application Ser. No. 11/134,870, now U.S. Pat. No. 7,758,594, filed on May 20, 2005; the entire disclosures of each of which are expressly incorporated herein by reference.

FIELD OF THE INVENTION

The present invention relates generally to medical devices and methods, and more particularly to systems and associated methods for altering or destructing tissues and anatomical or other structures within the body of human or animal subjects for the purpose of treating diseases or disorders.

One example of a condition where it is desirable to lift, compress or otherwise remove a pathologically enlarged tissue is Benign Prostatic Hyperplasia (BPH). BPH is one of the most common medical conditions that affect men, especially elderly men. It has been reported that, in the United States, more than half of all men have histopathologic evidence of BPH by age 60 and, by age 85, approximately 9 out of 10 men suffer from the condition. Moreover, the incidence and prevalence of BPH are expected to increase as the average age of the population in developed countries increases.

The prostate gland enlarges throughout a man's life. In some men, the prostatic capsule around the prostate gland may prevent the prostate gland from enlarging further. This causes the inner region of the prostate gland to squeeze the urethra. This pressure on the urethra increases resistance to urine flow through the region of the urethra enclosed by the prostate. Thus the urinary bladder has to exert more pressure to force urine through the increased resistance of the urethra. Chronic over-exertion causes the muscular walls of the urinary bladder to remodel and become stiffer. This combination of increased urethral resistance to urine flow and stiffness and hypertrophy of urinary bladder walls leads to a variety of lower urinary tract symptoms (LUTS) that may severely reduce the patient's quality of life. These symptoms include weak or intermittent urine flow while urinating, straining when urinating, hesitation before urine flow starts, feeling that the bladder has not emptied completely even after urination, dribbling at the end of urination or leakage afterward, increased frequency of urination particularly at night, urgent need to urinate etc.

In addition to patients with BPH, LUTS may also be present in patients with prostate cancer, prostate infections, and chronic use of certain medications (e.g. ephedrine, pseudoephedrine, phenylpropanolamine, antihistamines such as diphenhydramine, chlorpheniramine etc.) that cause urinary retention especially in men with prostate enlargement.

Although BPH is rarely life threatening, it can lead to numerous clinical conditions including urinary retention, renal insufficiency, recurrent urinary tract infection, incontinence, hematuria, and bladder stones.

In developed countries, a large percentage of the patient population undergoes treatment for BPH symptoms. It has been estimated that by the age of 80 years, approximately 25% of the male population of the United States will have undergone some form of BPH treatment. At present, the available treatment options for BPH include watchful waiting, medications (phytotherapy and prescription medications), surgery and minimally invasive procedures.

For patients who choose the watchful waiting option, no immediate treatment is provided to the patient, but the patient undergoes regular exams to monitor progression of the disease. This is usually done on patients that have minimal symptoms that are not especially bothersome.

Surgical procedures for treating BPH symptoms include Transurethal Resection of Prostate (TURP), Transurethral Electrovaporization of Prostate (TVP), Transurethral Incision of the Prostate (TUIP), Laser Prostatectomy and Open Prostatectomy.

Minimally invasive procedures for treating BPH symptoms include Transurethral Microwave Thermotherapy (TUMT), Transurethral Needle Ablation (TUNA), Interstitial Laser Coagulation (ILC), and Prostatic Stents.

The most effective current methods of treating BPH carry a high risk of adverse effects. These methods and devices either require general or spinal anesthesia or have potential adverse effects that dictate that the procedures be performed in a surgical operating room, followed by a hospital stay for the patient. The methods of treating BPH that carry a lower risk of adverse effects are also associated with a lower reduction in the symptom score. While several of these procedures can be conducted with local analgesia in an office setting, the patient does not experience immediate relief and in fact often experiences worse symptoms for weeks after the procedure until the body begins to heal. Additionally all device approaches require a urethral catheter placed in the bladder, in some cases for weeks. In some cases catheterization is indicated because the therapy actually causes obstruction during a period of time post operatively, and in other cases it is indicated because of post-operative bleeding and potentially occlusive clot formation. While drug therapies are easy to administer, the results are suboptimal, take significant time to take effect, and often entail undesired side effects.

There have been advances in developing minimally invasive devices and methods for lifting and repositioning of tissues. For example, approaches have been proposed to displace and/or compress lobes of a prostate gland to receive pressure on and provide a less obstructed path through a urethra.

There remains, however, a need for the development of new devices and methods that can be used for various procedures where it is desired to alter or destruct the lobes of a prostate in a minimally invasive manner. In particular, there is a need for alternative apparatus and treatment approaches for the purpose of treating median lobes of a prostate. Various structures ensuring an effective interventional procedure have been found to be needed.

The present disclosure addresses these and other needs.

SUMMARY

Briefly and in general terms, the present invention is directed towards an apparatus and method for treating the prostate. In one particular embodiment, structure is provided to accomplish desired destruction or alteration of a lobe of a prostate. A treatment device is provided to access the anatomy targeted for the interventional procedure, such as a median lobe. The treatment device facilitates the delivery of assemblies accomplishing destruction or alteration of tissue.

The treatment apparatus of the present disclosure includes various subassemblies which are mobilized via an actuator or other manually accessible structure. The operation of the subassemblies is coordinated and synchronized to ensure accurate and precise delivery.

In one particular aspect, the present invention is directed towards a treatment device which accomplishes the delivery of structures that accomplish the destruction or alteration of prostatic tissue. The procedure can be viewed employing a scope inserted in the device. Also, the delivery device can be sized and shaped to be compatible inside a sheath up to 24F, preferably a 19F sheath or smaller.

Various alternative methods of use are contemplated. The disclosed apparatus can be used to improve flow of a body fluid through a body lumen, modify the size or shape of a body lumen or cavity, treat prostate enlargement, or treat urinary incontinence, and/or treat various other disorders where a natural or pathologic tissue or organ is pressing on or interfering with an adjacent anatomical structure.

In a specific application, the disclosed apparatus are contemplated to be employed to destruct or alter an enlarged median lobe of a prostate. In one aspect, a treatment device is inserted into a prosthetic urethra transurethrally and the device is employed to destroy or alter the median lobe. Further, the system can additionally include an ultrasound or other imaging probe.

In another aspect, the delivery device housing the assembly is first guided into an ejaculatory duct of a patient. The assembly is then deployed from the ejaculatory duct to treat the median lobe so that it can be destroyed or altered. In yet a further aspect, an anterior approach can be taken such that tissue on an opposite side of the urethra to that of the median lobe is treated to open the urethra.

Various structures can be employed to engage and capture prostatic median lobe tissue. Moreover, various energies such as microwave or RF energy can be employed to destroy tissue along with or independent of capturing tissue with other devices. In particular, rotatable or expandable blades, articulating cutters, and pinchers can be configured to engage and capture tissue. Further, blunt dissectors with or without blades can be utilized for accessing tissue and performing other treatments.

Other features and advantages of the present invention will become apparent from the following detailed description, taken in conjunction with the accompanying drawings, which illustrate, by way of example, the principles of the invention.

BRIEF DESCRIPTION OF THE DRAWINGS

FIG. 15 is a partial cross-sectional view, depicting a curved blade for capturing material;

FIG. 16 is a partial cross-sectional view, depicting a tissue engaging structure including articulating arms;

FIGS. 17A-B are side views, depicting an expandable blade device;

FIG. 22 is a partial cross-sectional view, depicting a pinching device;

FIGS. 23A-B are partial cross-sectional views, depicting cutting and stapling prostatic tissue.

DETAILED DESCRIPTION OF THE PREFERRED EMBODIMENTS

Turning now to the figures, which are provided by way of example and not limitation, the present disclosure is directed to a device configured to deliver an anchor assembly within a patient's body for treatment purposes. The disclosed apparatus can be employed for various medical purposes including but not limited to destructing or altering tissues, organs, anatomical structures, grafts or other material found within a patient's body. Such approaches are intended to facilitate the treatment of diseases or disorders such as the displacement, compression and/or retraction of the median lobe of a prostate.

With reference to FIGS. 1-4, various features of urological anatomy of a human subject are presented. The prostate gland PG is a walnut-sized muscular gland located adjacent the urinary bladder UB. The urethra UT runs through the prostate gland PG. The prostate gland PG secretes fluid that protects and nourishes sperm. The prostate also contracts during ejaculation of sperm to expel semen and to provide a valve to keep urine out of the semen. A capsule C surrounds the prostate gland PG.

The urinary bladder UB holds urine. The vas deferentia VD define ducts through which semen is carried and the seminal vesicles SV secrete seminal fluid. The rectum R is the end segment of the large intestine and through which waste is dispelled. The urethra UT carries both urine and semen out of the body. Thus, the urethra is connected to the urinary bladder UB and provides a passageway to the vas deferentia VD and seminal vesicles SV.

Further, the trigone T (See FIG. 3) is a smooth triangular region of the bladder. It is sensitive to expansion and signals the brain when the urinary bladder UB is full. The verumontanum VM is a crest in the wall of the urethra UT where the seminal ducts enter. The prostatic urethra is the section of the urethra UT which extends through the prostate.

Figure 1:
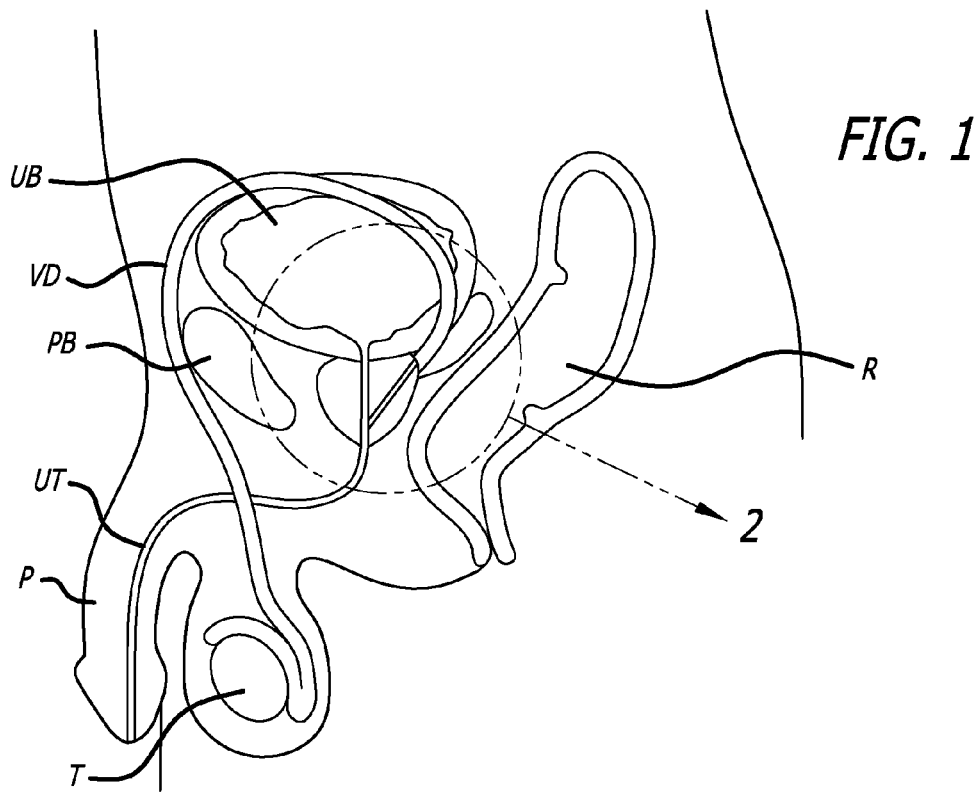
FIG. 1 is a cross-sectional view, depicting anatomy surrounding a prostate in a human subject.
Figure 2:
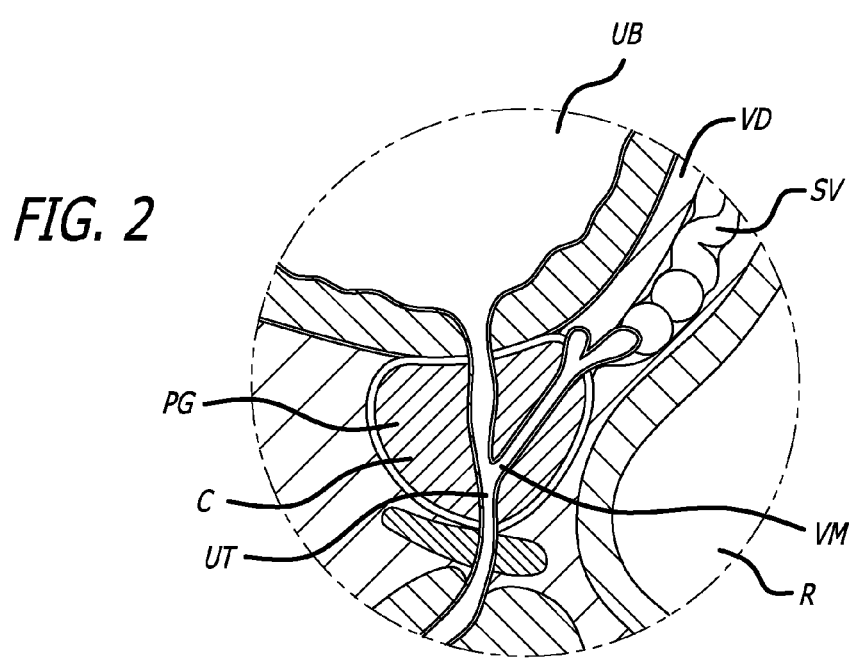
FIG. 2 is an enlarged cross-sectional view, depicting anatomy surrounding a prostate.
Figure 3:
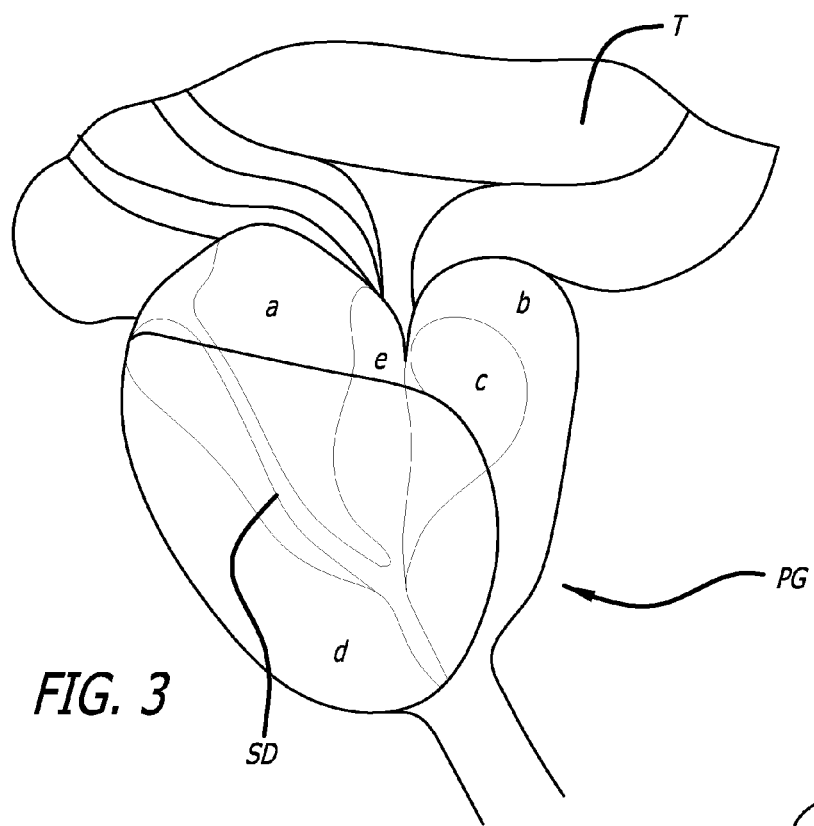
FIG. 3 is a schematic view, depicting prostatic anatomy zones.
Figure 4:
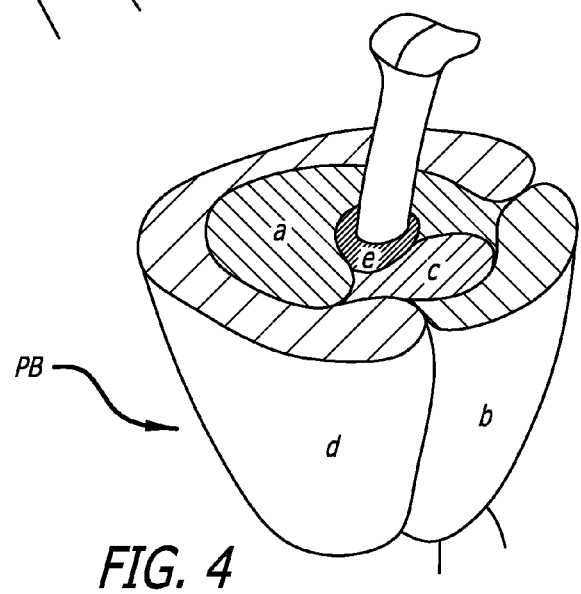
FIG. 4 is a schematic cross-sectional view, depicting further details of the anatomy zones shown in FIG. 3.

The prostate gland can be classified by zones or described by referring to its lobes (See FIG. 4). Whereas the zone classification is typically used in pathology, the lobe classification is more often used in anatomy. The central zone (a) of a prostate gland PG is about 25% of a normal prostate and this zone surrounds the ejaculating ducts. There is some prevalence of benign prostate hyperplasia in the transition zone. The fibromuscular zone (b) is usually devoid of glandular components and as its name suggests, is composed of only muscle and fibrous tissue. The transitional zone (c) generally overlays the proximal urethra and is the region of the gland that grows throughout life. Also, this lobe is often associated with the condition of benign prostatic enlargement. Finally, the peripheral zone (d) is the sub-capsular portion of the posterior aspect of the prostate gland that surrounds the distal urethra.

The lobe characterization is different from the zone characterization, but there is some overlap. The anterior lobe is devoid of glandular tissue and is completely formed of fibromuscular tissue. This lobe thus roughly corresponds to the anterior portion of the transitional zone (c). The posterior lobe roughly corresponds to the peripheral zone (d) and can be palpated through the rectum during a digital rectal exam. The posterior lobe is the site of 70-80% of prostatic cancers. The lateral lobe is the main mass of the prostate and is separated by the urethra. It has been described as spanning all zones. Lastly, the median lobe roughly corresponds to part of the central zone. It varies greatly in size and in some cases is devoid of glandular tissue.

A large or enlarged median lobe can act as a ball valve, blocking the bladder neck. Various approaches are contemplated to address such a condition. Thus, it is contemplated that the median lobe can be compressed, displaced and/or retracted to eliminate or decrease the blocking of the bladder neck.

Figure 5:
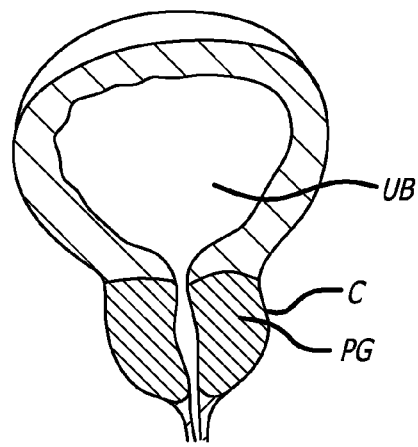
FIG. 5 is a cross-sectional view, depicting a normal prostate.
Figure 6:
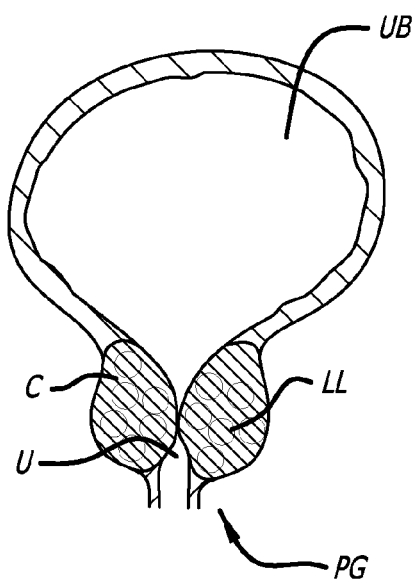
FIG. 6 is a cross-sectional view, depicting a prostate with enlarged lateral lobes.
Figure 7:
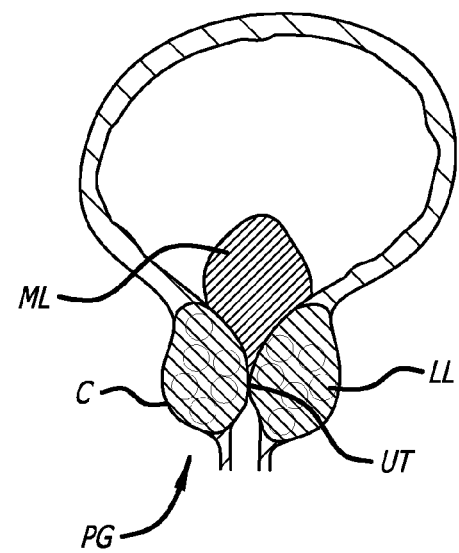
FIG. 7 is a cross-sectional view, depicting a prostate with enlarged lateral lobes and an enlarged median lobe.

Turning now to FIGS. 5-7, there are shown various prostate glands in cross-section. FIG. 5 depicts the urinary bladder UB and prostate gland PG of a healthy subject. FIG. 6 illustrates an individual with a prostate having enlarged lateral lobes LL and FIG. 7 depicts a subject suffering from both enlarged lateral lobes LL and an enlarged median lobe ML. It is to be appreciated that such enlarged anatomy impinges on the urethra UT and affects normal functioning. The following devices and approaches are intended to be employed to free up a path through the prostatic urethra.

Figure 8A:
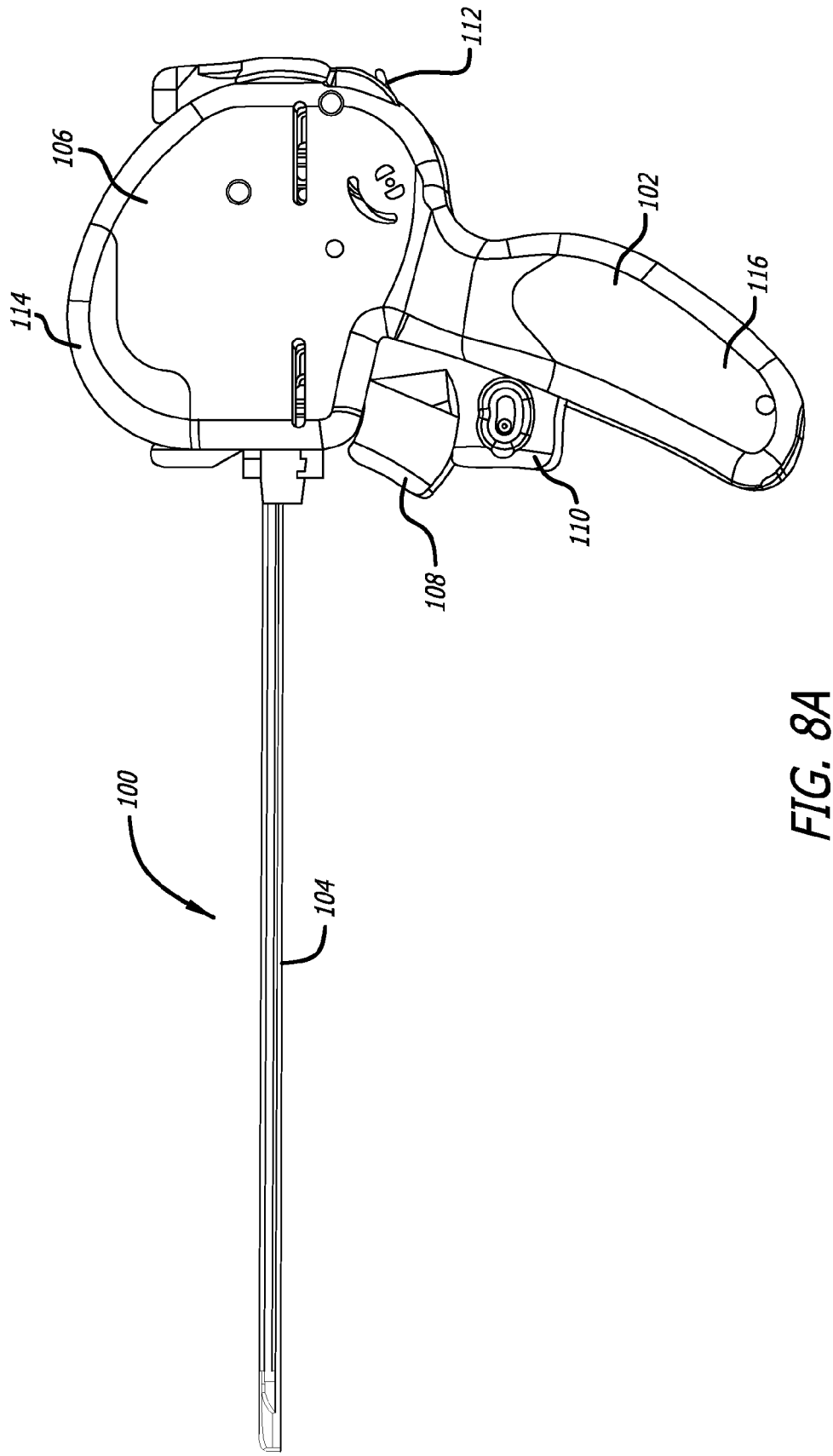
FIGS. 8A-C are side and perspective views, depicting one embodiment of a delivery device and various features thereof.
Figure 8B:
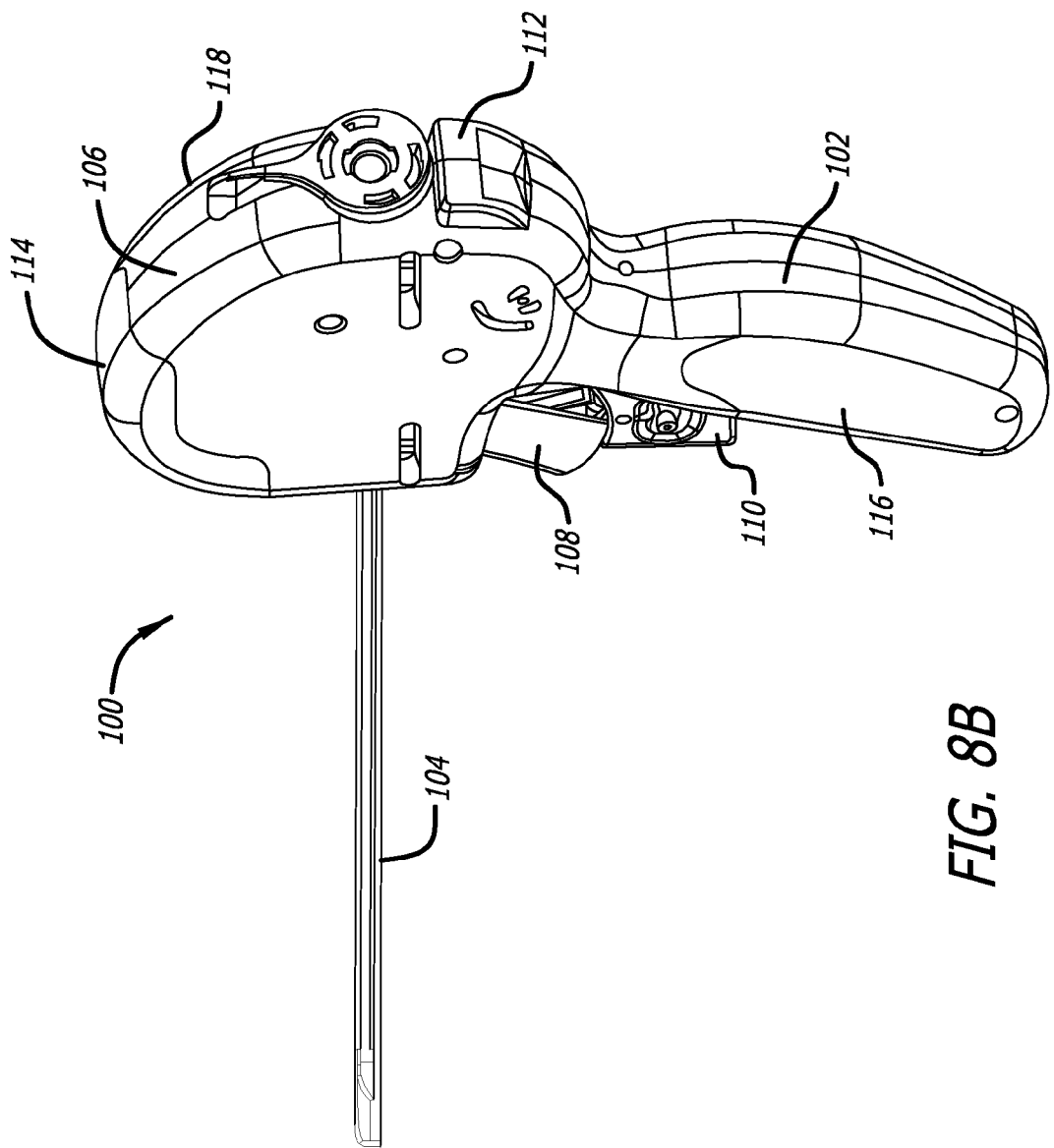
Figure 8C:
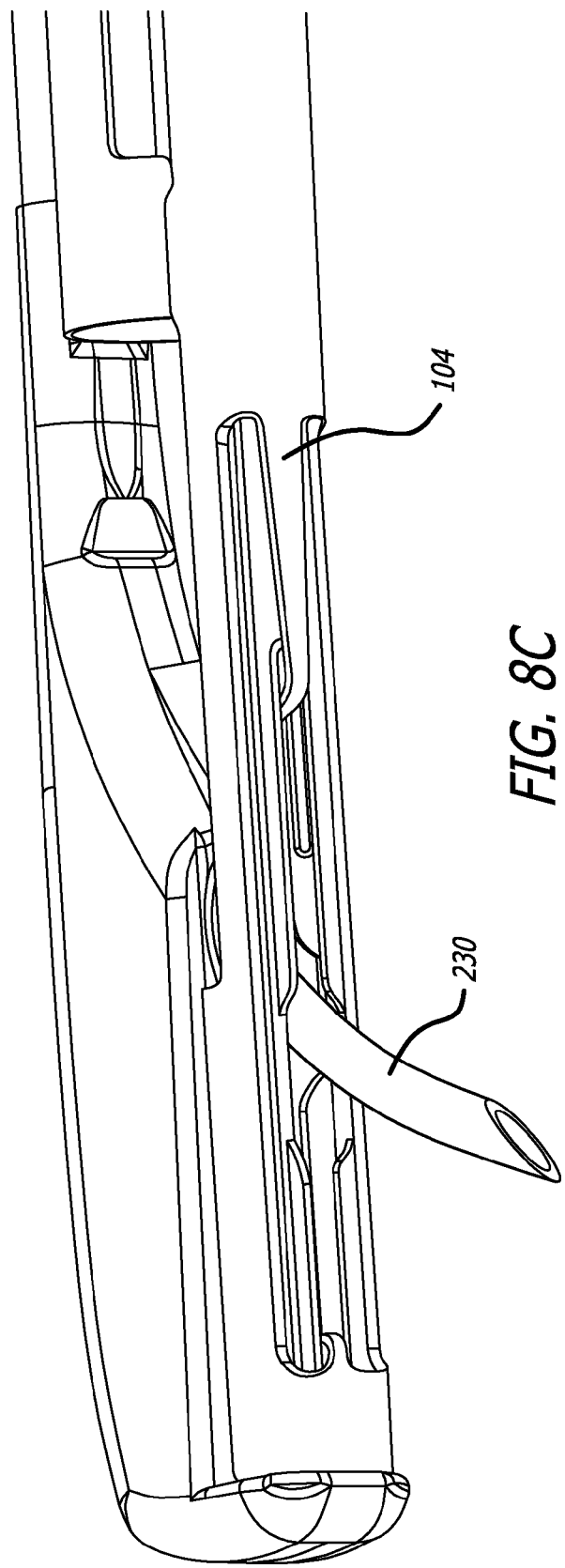

Referring now to FIGS. 8A-C, there is shown one embodiment of a treatment device 100. This device is configured to include structure that is capable of both gaining access to an interventional site as well as advancing structure into the prostate to accomplish the desired destruction of prostatic tissue. The device is further contemplated to be compatible for use with a 19F sheath. The device additionally includes structure configured to receive a remote viewing device (e.g., an endoscope) so that the steps being performed at the interventional site can be observed.

Prior to use of the present device 100, a patient typically undergoes a five day regiment of antibiotics. A local anesthesia can be employed for the interventional procedure. A combination of an oral analgesic with a sedative or hypnotic component can be ingested by the patient. Moreover, topical anesthesia such as lidocaine liquids or gel can be applied to the bladder and urethra.

The treatment device 100 includes a handle assembly 102 connected to an elongate tissue access assembly 104. The elongate tissue access assembly 104 houses components employed to destruct or alter a prostatic lobe and is sized to fit into a 19F cystosopic sheath for patient tolerance during a procedure in which the patient is awake rather than under general anesthesia. The tissue access assembly is stiff to allow manual compression of tissue at an interventional site by leveraging or pushing the handle assembly 102.

The treatment device 100 further includes a number of subassemblies. A handle case assembly 106 including mating handle parts which form part of the handle assembly 102. The handle assembly 102 is sized and shaped to fit comfortably within an operator's hand and can be formed from conventional materials. Windows can be formed in the handle case assembly 106 to provide access to internal mechanisms of the device so that a manual override is available to the operator in the event the interventional procedure needs to be abandoned.

In one embodiment, the treatment device 100 is equipped with various activatable members which facilitate delivery of tissue destruction or altering structure. A needle actuator 108 is provided and as described in detail below, effectuates the advancement of a needle assembly to an interventional site. In a preferred embodiment, the needle assembly has a needle that moves through a curved trajectory and exits the needle housing in alignment with a handle element, and in particular embodiments, in alignment with the grip. In various other embodiments, the needle housing is oriented such that the needle exits the housing at either the two o'clock or ten o'clock positions relative to a handle grip that is vertical. A needle retraction lever assembly 110 is also provided and when actuated causes the needle assembly to be withdrawn and expose tissue treatment structure. This action and the structure involved is also described in detail below.

In one particular, non-limiting use in treating a prostate, the elongate tissue access portion 104 of a treatment device is placed within a urethra (UT) leading to a urinary bladder (UB) of a patient. In one approach, the delivery device can be placed within an introducer sheath (not shown) previously positioned in the urethra or alternatively, the delivery device can be inserted directly within the urethra. The patient is positioned in lithotomy. The elongate portion 104 is advanced within the patient until a leading end thereof reaches a prostate gland (PG). In a specific approach, the side(s) (i.e., lobe (s)) of the prostate to be treated is chosen while the device extends through the bladder and the device is turned accordingly. The distal end of the elongate portion can be used to depress the urethra into the prostate gland by compressing the inner prostate tissue. The inside of the prostate gland (i.e., adenoma) is spongy and compressible and the outer surface (i.e., capsule) of the prostate gland is firm. By the physician viewing with an endoscope, he/she can depress the urethra into the prostate gland compressing the adenoma and creating the desired opening through the urethra. To accomplish this, the physician rotates the tool. The physician then pivots the tool laterally about the pubic symphysis PS relative to the patient's midline.

As shown in FIGS. 8A-B, the treatment device is at this stage configured in a ready state. The needle actuator 108 and the needle retracting lever 110 are in an inactivated position.

Upon depression of the needle actuator 108, the needle assembly 230 is advanced from within the elongate member 104 (See FIG. 8C). The needle can be configured so that it curves back toward the handle as it is ejected. In use in a prostate intervention, the needle assembly is advanced through and beyond a prostate gland (PG). Spring deployment helps to ensure the needle passes swiftly through the tough outer capsule of the prostate without "tenting" the capsule or failing to pierce the capsule. In one approach, the needle is made from Nitinol tubing and can be coated with Parylene N. Such a coating helps compensate for frictional or environmental losses (i.e. wetness) which may degrade effectiveness of needle penetration.

After complete depression of the needle actuator 108 and the unlocking of the needle retraction lever 110, the needle retraction lever 110 can be actuated. Such action results in a withdrawal of the needle assembly 230. In one embodiment, the needle 230 is withdrawn further than its original position within the device pre-deployment.

Figure 9A:
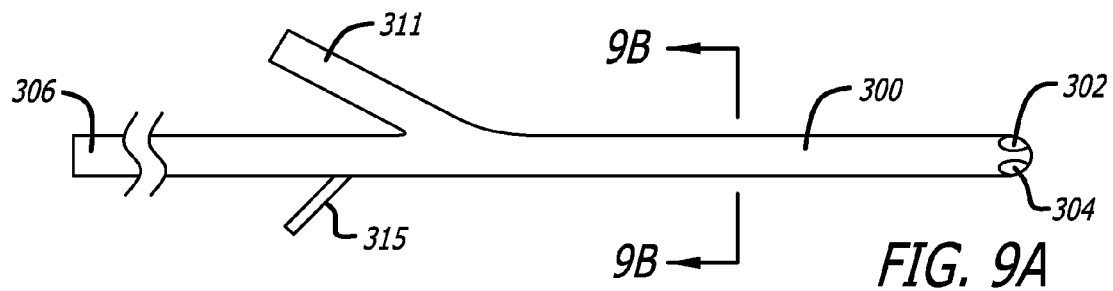
FIGS. 9A-C are side and cross-sectional views, depicting another embodiment of a delivery device.
Figure 9B:
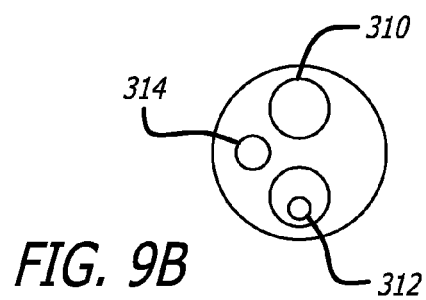
Figure 9C:
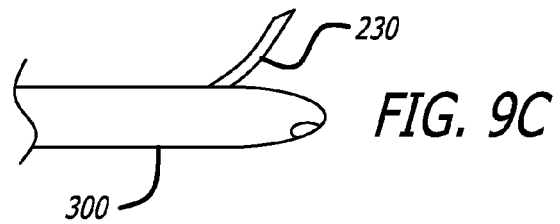

As an alternative, the treatment device can be defined by an elongate catheter 300. A distal end of the catheter 300 can include two openings, one opening 302 for a working device and a second opening 304 for vision and light. A proximal end 306 of the catheter can be adapted to connect to one or more of a light source and a camera. Extending along a length of the catheter 300 (See FIG. 9B) can be three or more lumens. There can be a first working lumen 310 in communication with the working device opening 302 and a working device channel 311. A second lumen 312 can be sized and shaped to receive camera optics (fibers) and light source fibers connected to the proximal end 306 and can extend to the second distal opening 304. Finally, a third lumen 314 can be provided to extend from a irrigation part 315 to a point near the distal end of the device (not shown). In another embodiment, the working device opening 302 can be moved proximally (See FIG. 9C) so that a working device such as a needle 230 can be extended from a side of the treatment device 300, and perhaps more directly into target tissue.

Figure 10A:
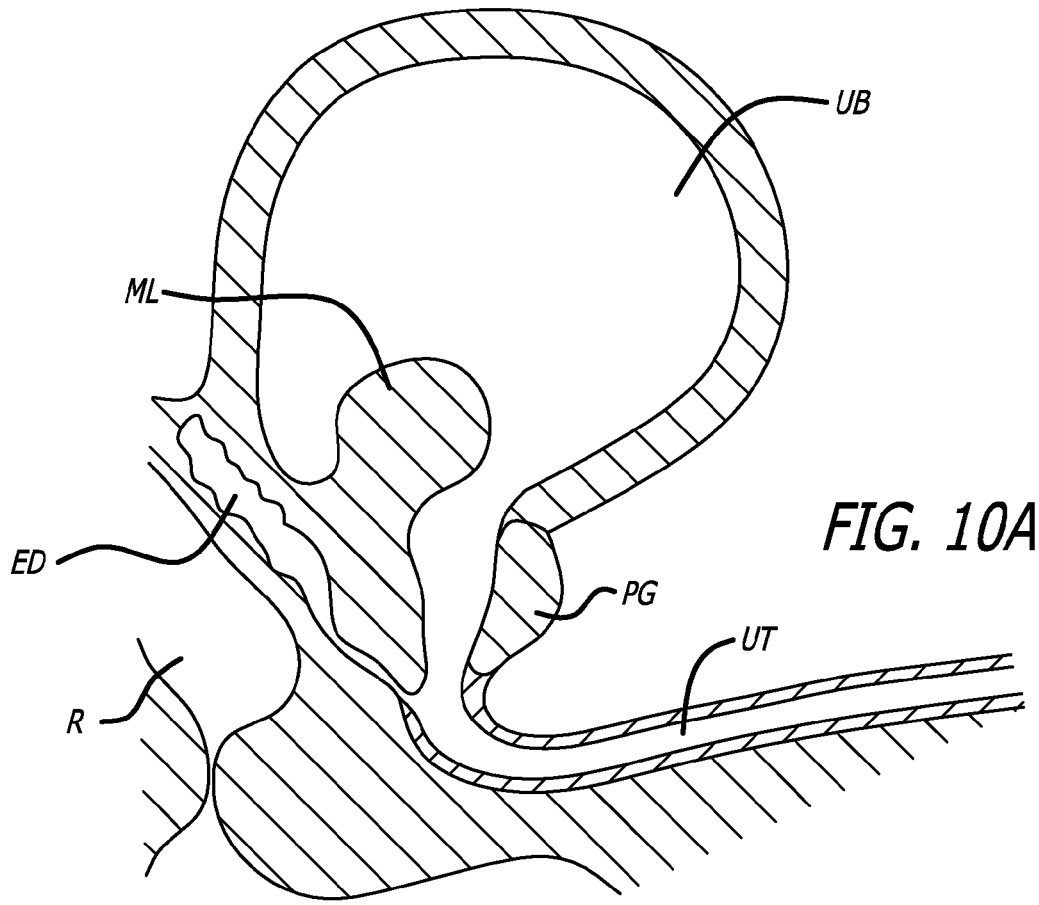
FIGS. 10A-B are cross-sectional views, depicting anatomy inflicted with an enlarged median lobe.
Figure 10B:
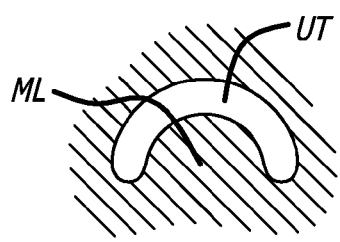

Turning now to FIGS. 10A-B, an approach to treating patients with median lobe ML disease is presented. Such an approach can be used as a complementary therapy with separate treatments for lateral lobes or can be employed to solely treat a median lobe ML. Because an enlarged median lobe ML can extend into the urinary bladder UB and may act as a ball valve interfering with normal function (See FIGS. 10A and 10B; FIG. 10B is a view through the prostatic urethra and into the urinary bladder), special consideration to moving tissue away from a ball valve location may facilitate accomplishing optimal results. The purpose here being to provide a less invasive means to treat median lobe hypertrophy as compared to TURP and TUIP (transurethral incision of the prostate). By avoiding such invasive approaches, there is minimal risk of disrupting the smooth muscle of the bladder neck and nerve tissue, ejaculating function and continence complications will likely be lower. BPH is a very prevalent disease that dramatically affects the quality of life of older men. About 30% of these men have a median lobe that creates a ball-valve effect. The presently disclosed procedure can significantly improve the urinary symptoms of these patients with a much better side effect profile. However, certain previously contemplated procedures currently require patient screening in order to exclude some patients with median lobes requiring treatment because these patients do not respond as readily to the therapy. Because current medical therapy may not be effective on median lobes, these patients only have resection/ablation as available options which both carry significant side effects. Thus, there exists a need to treat patients with median lobes without the significant side effect profile due to resection or ablation.

Figure 11:
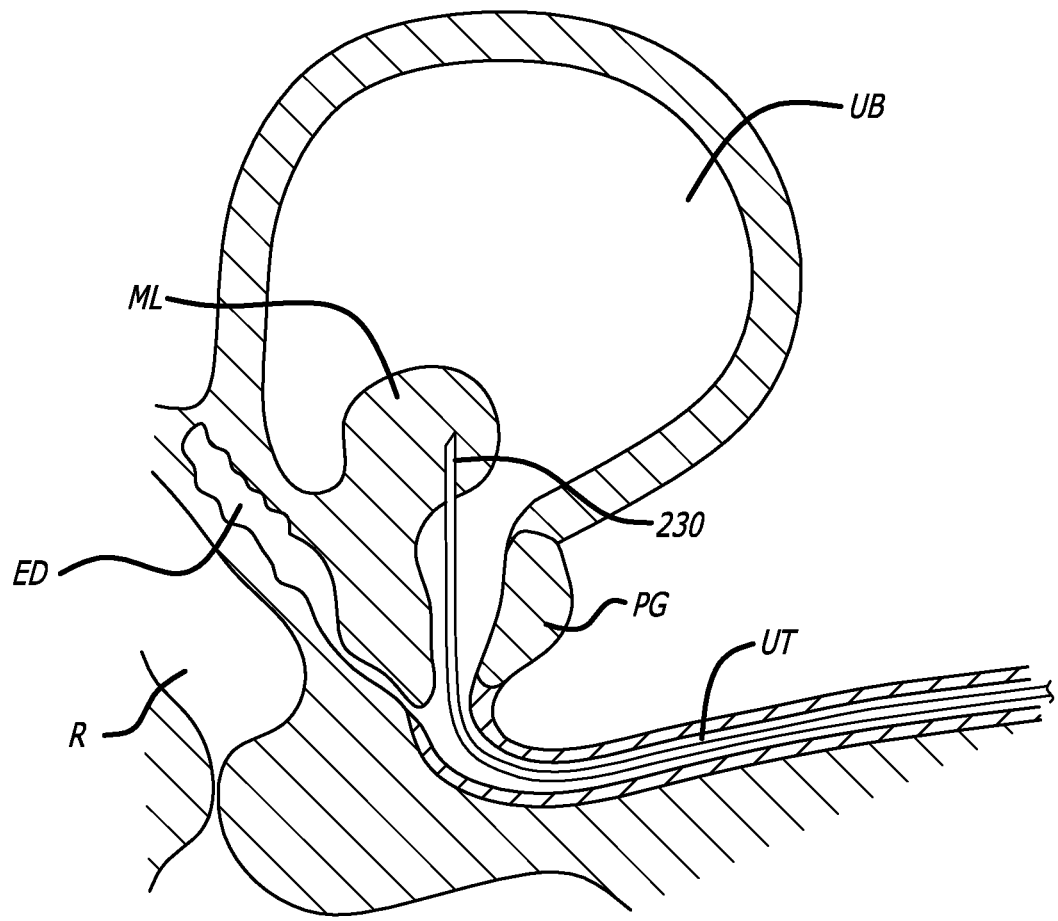
FIG. 11 is a cross-sectional view, depicting accessing a median lobe from a urethra.

As an initial step, sagittal views of a patient's bladder and prostate can be taken using transabdominal or transrectal ultrasonography. In this way, the patient's anatomy can be assessed. In this regard, an intravesical prostate measurement is taken to determine the vertical distance from a tip of the median lobe protrusion to the base of the bladder. After assessing the anatomy, the elongate tissue access assembly of a treatment device (See FIGS. 8-9C) can be advanced within the urethra UT (See FIG. 11). Various approaches to altering the prostate gland can then be undertaken.

While current treatments may be focused on lateral lobes of the prostate, patients with median lobe disease might get improved outcomes with a complementary therapy designed specifically for the median lobe. Because the median lobe may extend into the bladder and may act as a ball valve, special consideration to creating a channel via a tunnel may be advantageous for optimal results. In one approach, it is contemplated that a passageway through the median lobe can be created to allow urine to pass. A tunnel through the prostate median lobe can be produced by creating a passageway through the median lobe which allows urine to pass from the bladder into the urethra. In this concept, the passageway can be created by either removing tissue or displacing tissue. Specifically, removing tissue to produce the tunnel could be done using any of the ablation techniques available (e.g. RF Energy, Lasers, etc.). With regard to displacing tissue, an implant in the form of a suture or a cylindrical shaped tunnel or mesh may be implanted in the median lobe.

Thus, in this way, a passageway for urine to flow is provided even when the median lobe acts as a ball valve and "closes" on the bladder neck. Moreover, due to a transurethral delivery approach, minimal tissue is either being removed or displaced to create this passageway. This leads to minimal patient discomfort, scarring, and general complications. This concept is less invasive than current minimally invasive therapies (TUMT, TUNA, TUIP and TURP). Accordingly, by reducing the amount of tissue removed there is minimal risk of disrupting the smooth muscle of the bladder neck and nerve tissue, ejaculatory function and continence complications will likely be lower than these other noted therapies.

After accessing the prostate using the treatment device described above, the median lobe can be injected with a pharmacological agent or drug, such as the Botulinum Toxin. The drug mechanisms could include relaxation of the smooth muscle tissue such that the median lobe would not retain its shape and seal to the bladder neck and local apoptosis of median lobe cells can ensue. Apoptosis could result in shrinkage of the median lobe or change in shape of the median lobe such that obstruction of the bladder neck opening is reduced. Small needles and relatively few injections sites could be employed as ways to reduce pain to the patient. The injections could also be potentially administered using flexible cystoscopy, so that damage to the urethra is minimal. This approach involves fast treatment times, a low level of pain for the patient if small needles are suitable, and the use of minimally-invasive, flexible cystoscopy. As an alternative, drugs can be injected in the area around the median lobe. Pharmacological agents could also be administered to the median lobe through the perineum or rectum.

Figure 12:
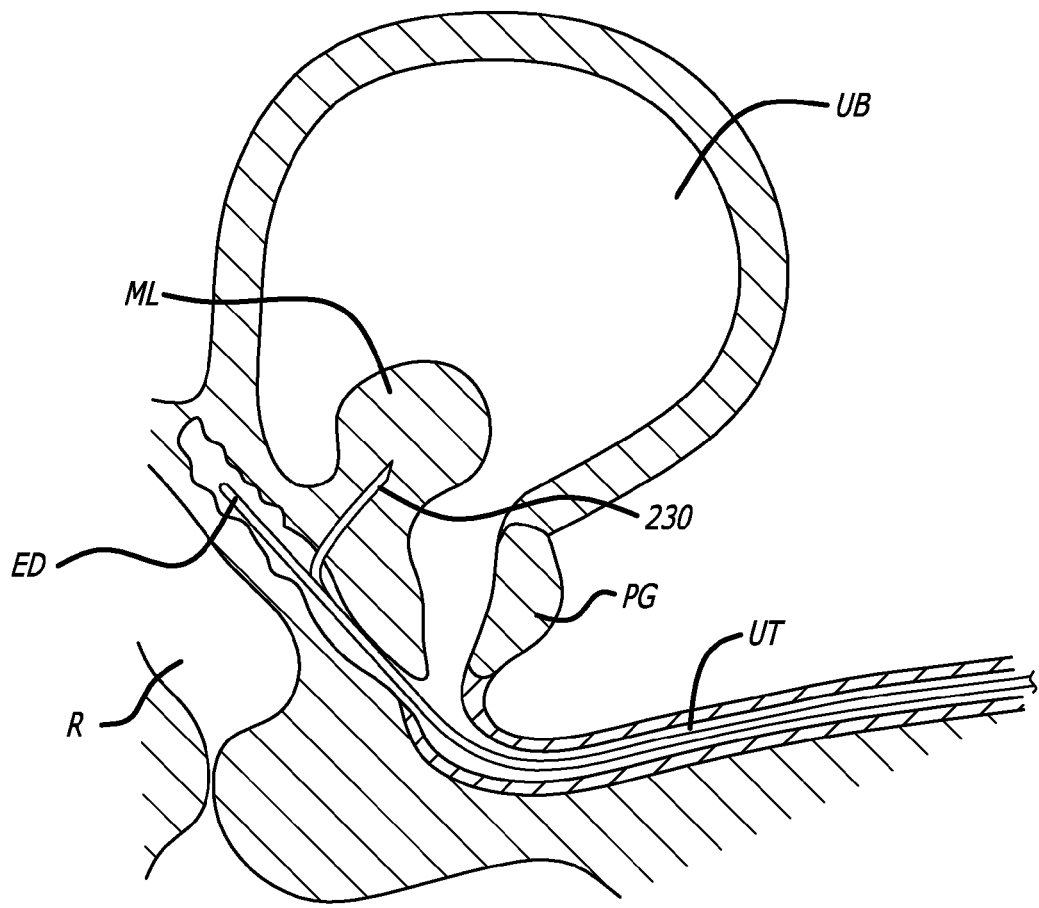
FIG. 12 is a cross-sectional view, depicting accessing a median lobe from an ejaculatory duct.
Figure 13:
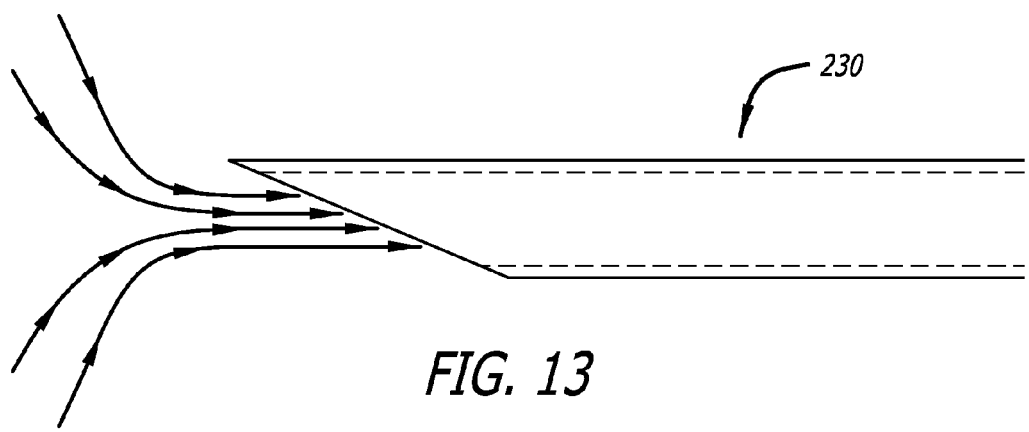
FIG. 13 is a side view, depicting suction for capturing material.

In yet another approach, the catheter or treatment device is inserted into the urethra and guided into the ejaculatory duct ED (See FIG. 12). A needle 230 is advanced into the enlarged median lobe ML. The needle 230 can be used to remove tissue from the median lobe via a vacuum (See FIG. 13) from within the median lobe. The volume of the enlarged median lobe is reduced, lowering the obstruction of the bladder neck and urethra UT. As the trans-ejaculatory duct ED delivery scheme and needle stick are minimally invasive urethral tissue is preserved. Further, there may be no need for implant materials. It is to be recognized that a vacuum can be used to remove tissue once the median lobe is accessed from other routes as well.

The contemplated approaches could be used in conjunction with a primary device or catheter in the urethra/bladder neck and a secondary catheter or device in the ejaculatory duct to treat the median lobe. The idea of approaching the median lobe from the anterior and posterior sides may increase an ability to locate and treat it. The median lobe could be treated with smaller devices from both the bladder side and the ejaculatory duct side, via multiple smaller vacuum needles, cryoablation treatments, or heating treatments (radiofrequency, microwave, laser, etc). The catheter or device may be flexible, rigid or semi-rigid. The needle may exit at the tip of the device, or may exit at the side of the device. Some portion or the entire catheter or device may have articulation control to allow for navigating and positioning.

In one specific application, the treatment catheter may be employed to freeze tissue via direct injection of a freezing agent, like liquid nitrogen, into the tissue. The freezing may be achieved via thermal conduction through the needle. The needle 230 may be a material with high thermal conductivity. The inner diameter ID of the needle may contain a cryogenic agent, liquid nitrogen, rapidly expanding gas, or other. The needle may further contain a temperature probe (not shown) to allow a feedback loop to a control system to control the size and volume of tissue to be frozen. The needle may exit the distal end of the catheter, or may exit the side of the treatment catheter. The catheter may be flexible, rigid or semi-rigid. Again, some portion or the entire catheter may have articulation control to allow for navigating and positioning.

Figure 14:
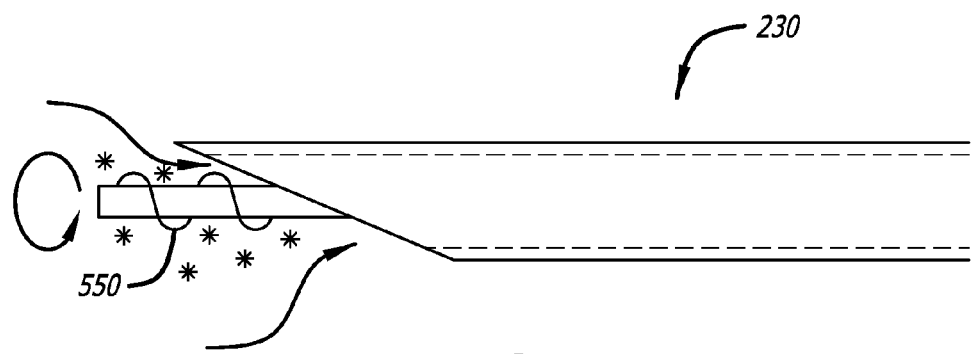
FIG. 14 is a side view, depicting a rotating blade for capturing material.

In another specific example (See FIG. 14), the catheter may contain a rotating helical blade 550 which is advanced out of a working channel or needle 230, and cuts tissue, assisting in tissue removal with or without a vacuum assistance. Again, the catheter may be flexible, rigid or semi-rigid. The working channel may exit at the tip of the device, or may exit at the side of the device. Some portion or the entire catheter also may have articulation control to allow for navigating and positioning. Additionally, an RF generator can be included for cauterization after tissue removal.

Such a device could be stand-alone, i.e. not requiring a TRUS probe. The device could accommodate insertion of an ultrasound or other imaging probe into the device for guidance and could have an integrated disposable imaging system. A handle on the needle device can be added to fully or partially automate delivery. The handle can have user settings for needle depth. The needle depth can be fixed in the manufacturing factory and available in different lengths to the market. The user can then select the appropriate length based on TRUS or other imaging data. Also, the needle can be coated or doped with antimicrobial materials such as silver. A Foley catheter or other device could be used to locate the urethra on the TRUS image. In fact, a customized Foley catheter could provide a specific deployment target and a Doppler flow feature on the ultrasound could be sued in conjunction with a Foley catheter to further enhance the target.

Turning now to FIGS. 15-19B, various other structure are presented for removing tissue from a lobe of a prostate. As shown in FIG. 15, the tissue altering or removing structure can be embodied in a linearly activated blade 560. The blade 560 can have a curved distal end, with a hollowed out receptacle that facilitates scooping of tissue. The tissue removing structure can also be embodied in a grasper assembly 570 (FIG. 16). The grasper assembly 570 can include articulating arms 572 with inwardly directed blade tips 574. Both structures are sized and shaped to be advanceable through the treatment device, and can in particular, be extendable from and through a needle 230. As shown in FIGS. 17A-B, tissue removing structures can also be defined by an elongate member with a distal end defined by an expandable cutting member 580.

Figure 18A:
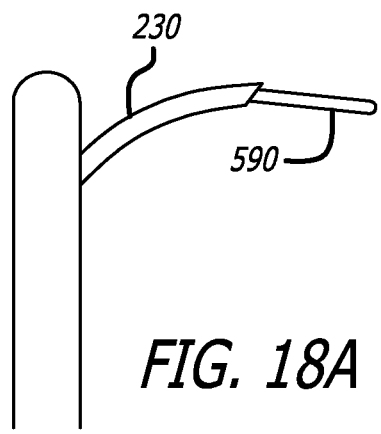
FIGS. 18A-B are side views, depicting blunt dissector devices.
Figure 18B:
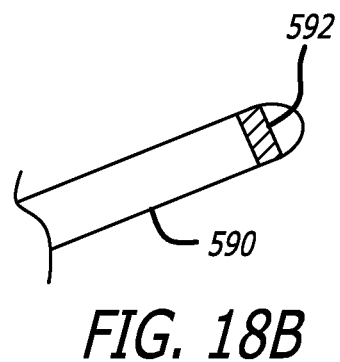

With reference to FIGS. 18A-B, the treatment device can further include an extending blunt dissecting tip 590. A penetrating tip is extended a specified amount to penetrate the tissues near the device (e.g. urethra, prostate tissue and capsule) and the blunt dissector 590 is used to extend the access in an atraumatic way along the tissue planes that were first accessed using the penetrating tip. The needle or penetrating tip may be extended to a pre-determined distance or using a pre-determined force in order to sufficiently penetrate the desired tissues. It could be advanced via hand, spring, electrical, or pneumatic power and could be controlled via electrical or other feedback from the tissue near the distal tip of the penetrating tip. The blunt dissector 590 may be of tuned flexibility with a flexible tip that can buckle over to provide a large atraumatic radius for tissue dissection. Either or both parts of the device could be fabricated of implant-grade materials and could be separated from the treatment device. One means for this is a wire-like device that is inserted and buckles and fold upon resistance such that it forms a knob or nest which is larger than the access hole and therefore resists pullout through the access hole. An electrical system could be added to the system such that penetration of a nearby organ (e.g. bladder or rectum) could be detected by the completion of an electrical circuit. In this regard, a conductive strip 592 can be added to the blunt tip dissector 590.

Figure 19A:
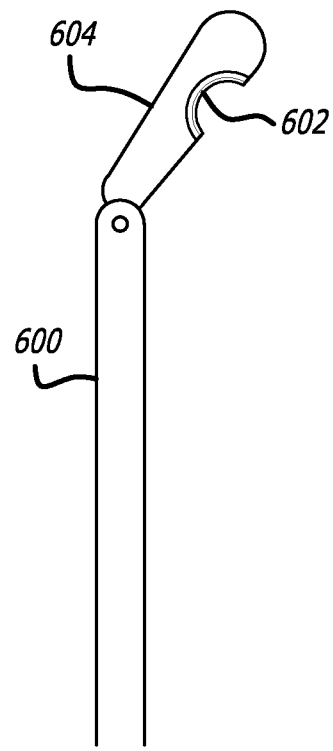
FIGS. 19A-B are side views, depicting dissectors including cutting blades.
Figure 19B:
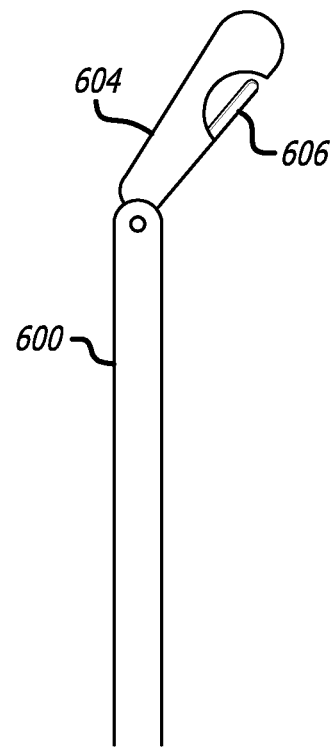

A dissector 600 can further or alternatively include an integral blade 602 positioned proximal a terminal end of the device as well as an articulating head 604 (FIG. 19A). Cutting action is provided by pivoting the articulation head. In place of the integral blade, the dissector can further include a retractable blade 606 (FIG. 19B) which can be translated to effect desired cutting action.

Figure 20:
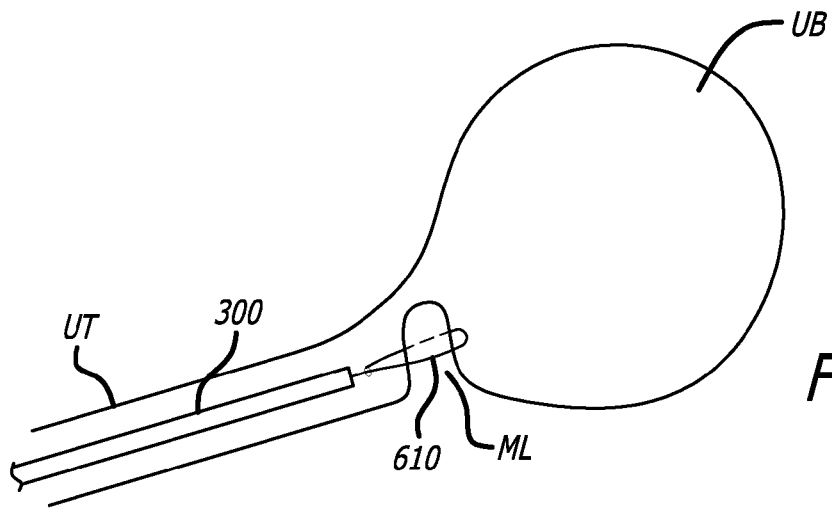
FIG. 20 is a partial cross-sectional view, depicting a noose device.

Still yet other approaches to remove median lobe tissue or reduce the median lobe volume are shown in FIGS. 20-23B. As shown in FIG. 20, a transurethral treatment device 300 can be used to apply a noose or ligature clip 610 around the median lobe ML. The noose or ligature clip 620 is left in place long enough to cause tissue necrosis. Once the median lobe separates from the patient, it would be either voided after catheter removal or removed during a second procedure. This approach involves no tissue cutting and could have minimal blood loss compared to conventional BPH surgical approaches. Important urological anatomy is undisturbed and erectile dysfunction and incontinence would potentially be lower than other BPH therapies.

Figure 21:
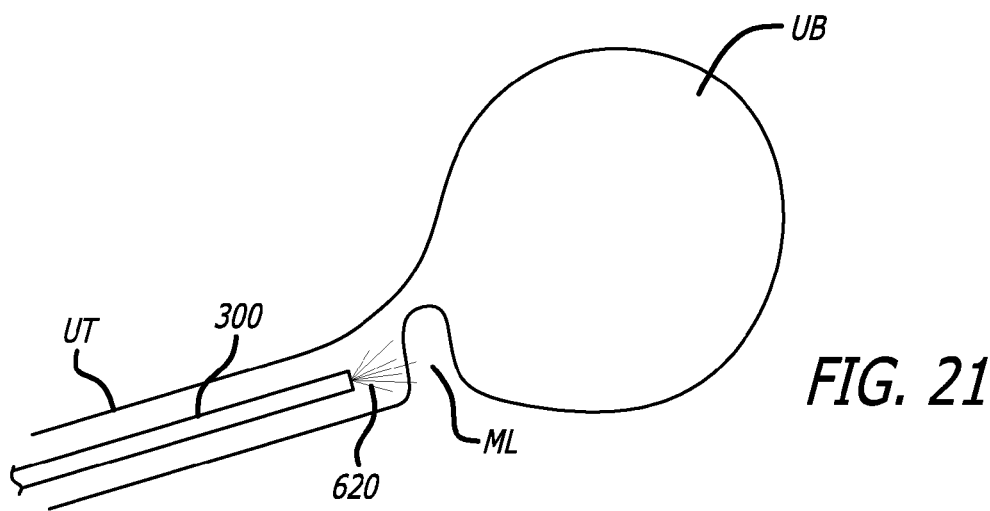
FIG. 21 is a partial cross-sectional view, depicting applying microwave energy to a median lobe.

A transurethral treatment device can also be employed to apply microwave energy 620 to the median lobe ML to cause tissue necrosis (See FIG. 21). Over time, the dead median lobe tissue would contract and allow improved urological function. Current TUMT technology and treatment techniques can thus be leveraged by applying microwave energy to the median lobe to kill and shrink the tissue to alleviate BPH symptoms. This would specifically target the median lobe and could prove to be a faster and less expensive procedure than current TUMT treatment modalities and be less traumatic to the patient.

A transurethral treatment catheter 300 including a translatable pincher 620 that pinches the median lobe ML to eliminate its blood supply. The catheter 300 is left in place long enough to cause tissue necrosis. Once the median lobe separates from the patient, it would be either voided after catheter removal or removed during a second procedure. As with the noose/ligature clip approach, this approach involves no tissue cutting and could have minimal blood loss compared to current BPH surgical approaches. Important urological anatomy is again undisturbed and erectile dysfunction and incontinence would potentially be lower than other BPH therapies.

Alternatively referring to FIGS. 22-23B, a transurethral treatment device 300 for removing median lobe ML tissue can include a cutting wire, ring or blade 640. The cutting wire, ring or blade 640 could have the means to electro-cauterize the tissue cut plane to minimize blood loss. The median lobe ML tissue could then be morsellized using a secondary device. As such, current electro-cauterizing tissue cutting technology to effectively remove the median lobe. Specially targeting the median lobe ML could prove to be a faster and less expensive procedure than current BPH treatment methods and be less traumatic to the patient. Structure can also be provided to simultaneously staple 650 and cut the enlarged median lobe ML. The severed median lobe tissue could be morsellized using a secondary device.

Figure 24A:
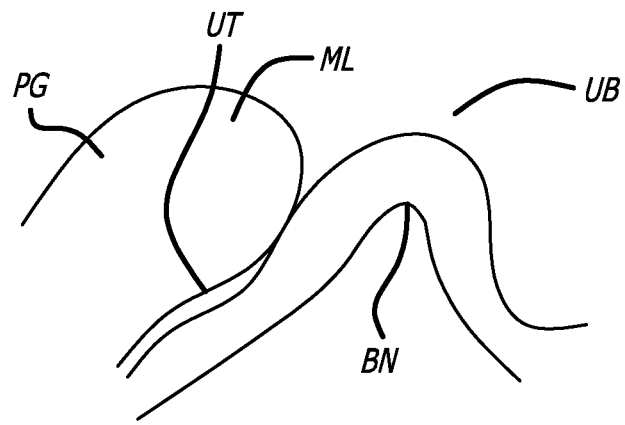
FIGS. 24A-B are partial cross-sectional views, depicting cutting tissue adjacent a bladder neck.
Figure 24B:
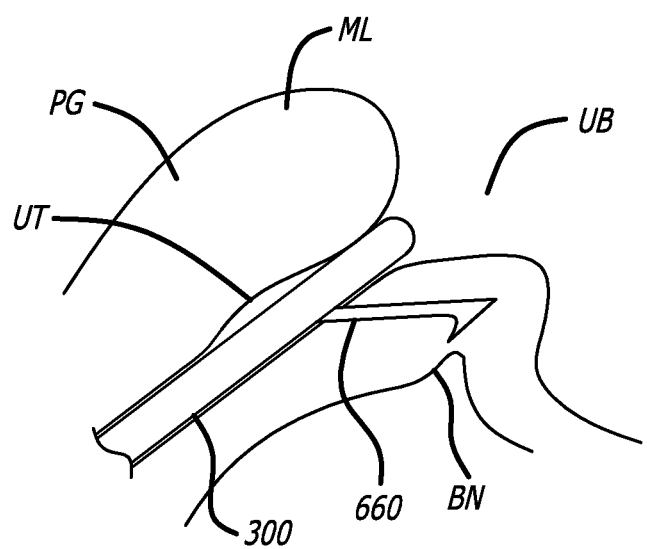

Finally, with reference to FIGS. 24A-B, rather than cut through the urethra UT and create an open wound exposed to urine, access to the bladder neck BN can be gained via a small puncture. Such a small puncture can be formed by a needle 660 and the same can be used to tunnel sub-epithelially to the bladder neck BN. Circular muscle of the bladder neck BN can then be cut to release the bladder neck BN. The bladder neck opening will thus relax and the obstructing median lobe ML or bladder neck adenoma will recede into newly released space away from the urethra UT. Such action reduces the valve pressure of the bladder neck obstruction.

It is to be recognized that the devices and methods disclosed herein can be used to treat a variety of pathologies in a variety of lumens or organs comprising a cavity or a wall. Examples of such lumens or organs include, but are not limited to urethra, bowel, stomach, esophagus, trachea, bronchii, bronchial passageways, veins (e.g. for treating varicose veins or valvular insufficiency), arteries, lymphatic vessels, ureters, bladder, cardiac atria or ventricles, uterus, fallopian tubes, etc.

Moreover, it is to be appreciated that the disclosure has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless to do so would render the embodiment or example unpatentable or unsuitable for its intended use. Also, for example, where the steps of a method are described or listed in a particular order, the order of such steps may be changed unless to do so would render the method unpatentable or unsuitable for its intended use. All reasonable additions, deletions, modifications and alterations are to be considered equivalents of the described examples and embodiments and are to be included within the scope of the following claims.

Thus, it will be apparent from the foregoing that, while particular forms of the invention have been illustrated and described, various modifications can be made without parting from the spirit and scope of the invention.

We claim:

1. A method for treating benign prostatic hypertrophy, comprising:
   assessing an anatomy of a median lobe;
   inserting a treatment device within a urethra, the treatment device includes an extendable needle and an elongate member advanceable through the extendable needle, wherein the elongate member includes a curved cutting blade;
   actuating the treatment device to advance the needle within the median lobe to form a penetration track; and
   advancing the elongate member beyond the needle while the needle is within the median lobe to capture, separate, cut, dissect and/or remove tissue of the median lobe.

2. The method of claim 1, further comprising advancing the treatment device into an ejaculatory duct.

3. The method of claim 1, further comprising applying energy to the median lobe to destroy tissue.

4. The method of claim 3, wherein the energy is microwave energy.

5. The method of claim 1, further comprising cauterizing median lobe tissue.

6. The method of claim 1, further comprising applying a vacuum to remove tissue from the median lobe.

7. The method of claim 1, wherein the elongate member includes a rotatable helical blade, further comprising rotation of the helical blade.

8. The method of claim 1, wherein the elongate member includes articulating cutting arms and further comprising articulating the arms to cut median lobe tissue.

9. The method of claim 1, wherein the elongate member includes an expandable cutter and further comprising expanding the cutter to cut median lobe tissue.

10. The method of claim 1, wherein the elongate member includes a blunt dissector and further comprising dissecting median lobe tissue with the dissector.

11. The method of claim 10, wherein the blunt dissector further includes a cutter blade.

12. The method of claim 1, wherein the elongate member includes a ligature and further comprising configuring the ligature about the median lobe.

* * * * *